United States Patent
Kajihara et al.

(10) Patent No.: US 10,913,763 B2
(45) Date of Patent: Feb. 9, 2021

(54) METHOD FOR PRODUCING SUGAR HAVING SULFATE GROUP AND/OR PHOSPHATE GROUP

(71) Applicant: GLYTECH, INC., Kyoto (JP)

(72) Inventors: Yasuhiro Kajihara, Osaka (JP); Akihiro Manbo, Osaka (JP); Takefumi Murase, Kyoto (JP)

(73) Assignee: GLYTECH, INC., Kyoto (JP)

( * ) Notice: Subject to any disclaimer, the term of this patent is extended or adjusted under 35 U.S.C. 154(b) by 193 days.

(21) Appl. No.: 16/078,861

(22) PCT Filed: Mar. 7, 2017

(86) PCT No.: PCT/JP2017/009106
§ 371 (c)(1),
(2) Date: Aug. 22, 2018

(87) PCT Pub. No.: WO2017/154938
PCT Pub. Date: Sep. 14, 2017

(65) Prior Publication Data
US 2020/0062794 A1    Feb. 27, 2020

(30) Foreign Application Priority Data

Mar. 9, 2016  (JP) .................. 2016-045534

(51) Int. Cl.
| | | |
|---|---|---|
| C08B 37/00 | (2006.01) | |
| C07H 11/00 | (2006.01) | |
| C07H 11/04 | (2006.01) | |
| C07H 1/00 | (2006.01) | |
| C07H 15/12 | (2006.01) | |
| C07H 15/203 | (2006.01) | |
| C07H 19/01 | (2006.01) | |

(52) U.S. Cl.
CPC .............. *C07H 15/12* (2013.01); *C07H 1/00* (2013.01); *C07H 11/00* (2013.01); *C07H 11/04* (2013.01); *C07H 15/203* (2013.01); *C07H 19/01* (2013.01); *C08B 37/0069* (2013.01); *C08B 37/0075* (2013.01)

(58) Field of Classification Search
None
See application file for complete search history.

(56) References Cited

U.S. PATENT DOCUMENTS

| | | | |
|---|---|---|---|
| 5,405,949 A | 4/1995 | Ungarelli et al. | |
| 5,410,039 A | 4/1995 | Ungarelli et al. | |
| 5,430,132 A | 7/1995 | Silvano et al. | |
| 2005/0004069 A1 | 1/2005 | Uzawa et al. | |
| 2005/0010044 A1 | 1/2005 | Linhardt et al. | |
| 2010/0121041 A1 | 5/2010 | Shoda et al. | |

FOREIGN PATENT DOCUMENTS

| | | |
|---|---|---|
| EP | 0465966 | 1/1992 |
| EP | 1408116 | 4/2004 |
| JP | H06065273 | 3/1994 |
| JP | H09263595 | 10/1997 |
| JP | 2001019698 | 1/2001 |
| JP | 2005232064 | 9/2005 |
| JP | 2007332226 | 12/2007 |
| JP | 2008007643 | 1/2008 |
| JP | 2014047155 | 3/2014 |
| WO | 2010/117803 | 10/2010 |
| WO | 2013/141350 | 9/2013 |
| WO | 2015/080603 | 6/2015 |

OTHER PUBLICATIONS

Nadanaka et al., "Characteristic Hexasaccharide Sequences in Octasaccharides Derived from Shark Cartilage Chondroitin Sulfate D with a Neurite Outgrowth Promoting Activity" Journal of Biological Chemistry vol. 273 No. 6 pp. 3296-3307 (Year: 1998).*
Tiruchinapally et al., "Divergent Heparin Oligosaccharide Synthesis with Preinstalled Sulfate Esters" Chemistry vol. 37 No. 36 pp. 10106-10112 DOI:doi:10.1002/chem.201101108 (Year: 2011).*
Jacquinet et al., "From Polymer to Size-Defined Oligomers: A Highly Divergent and Stereocontrolled Construction of Chondroitin Sulfate A, C, D, E, K, L, and M Oligomers from a Single Precursor: Part 2" Chem Eur J vol. 15 pp. 9579-9595 DOI: 10.1002/chem.200900741 (Year: 2009).*
International Search Report, PCT/JP2017/009106, dated Jun. 6, 2017, 3 pages.
Belot F et al. Chemoenzymatic synthesis of sulfated O-linked oligosaccharides: epitopes for MECA-79, Tetrahedron Letters. 2002; 43: 7743-7747.
Lubineau A et al. Chemoenzymatic synthesis of 3IV, 6III-disulfated Lewis pentasaccharide, a candidate ligands for human L-selectin. Carbohydrate Research. 1998, 305(3-4): 501-509.
Pratt MR and Bertozzi CR. Syntheses of 6-sulfo sialyl Lewis X glycans corresponding to the L-selectin ligand "sulfoadhesin", Organic Letters. 2004; 6(14): 2345-2348.
Yang W et al. Homoserine as an aspartic acid precursor for synthesis of proteoglycan clycopeptide containing aspartic acid and a sulfated glycan chain. Journal of Organic Chemlstry, 2016: 81(23): 12052-12059.

(Continued)

*Primary Examiner* — Eric Olson
(74) *Attorney, Agent, or Firm* — Myers Bigel, P.A.

(57) ABSTRACT

An object of the invention is to provide a method of uniformly and efficiently producing a saccharide having a sulfate group and/or a phosphate group in the molecule, or a compound containing the saccharide. [Solution] The present invention provides a method of producing a saccharide having a sulfate group and/or a phosphate group. The method comprises (a) a step of preparing a "first saccharide having a non-protected sulfate group and/or a non-protected phosphate group" and a "second saccharide having a non-protected sulfate group and/or a non-protected phosphate group" and (b) a step of condensing the first saccharide and the second saccharide prepared in the step (a) with each other.

23 Claims, No Drawings

(56) References Cited

OTHER PUBLICATIONS

Yoshida T et al. Synthesis of a set of di- and tri-sulfated galabioses. Carbohydrate Research. 2001; 335: 167-180.
Extended European Search report, Application No. 17763278.3, dated Jan. 22, 2020, 10 pages.
Wong et al "Synthetic glycosylation of peptides using unprotected saccharide beta-glycosylamines" Glycoconjugate Journal, 10:227-234 1993.
Herzner et al "(p-Sulfomethyl) phenylalanine as a mimic of O-sulfatyl-tyrosine in synthetic partial sequences of P-Selectin glycoprotein ligand 1 (PSGL-1)" Tetrahedron, 63(28):6423-6436 2007.
Lange et al. "Towards Keratan Sulfate-Chemoenzymatic Cascade Synthesis of Sulfated N-Acetyllactosamine (LacNAc) Glycan Oligomers" Advanced Synthesis & Catalysis., 358(4):584-596 (2016).
European Office Action corresponding to European Patent Application No. 17763278.3, dated Sep. 26, 2019, 7 pages.

* cited by examiner

METHOD FOR PRODUCING SUGAR HAVING SULFATE GROUP AND/OR PHOSPHATE GROUP

STATEMENT OF PRIORITY

This application is a 35 U.S.C. § 371 national phase application of International Application Serial No. PCT/JP2017/009106, filed Mar. 7, 2017, which claims the benefit, under 35 U.S.C. § 119 (a) of Japanese Patent Application No. 2016-045534, filed Mar. 9, 2016, the entire contents of each of which are incorporated by reference herein.

TECHNICAL FIELD

The present invention relates to a method of producing a saccharide having a sulfate group and/or a phosphate group, or a compound including the saccharide.

BACKGROUND ART

A saccharide containing a sulfate group in the molecule is known to have various physiological effects. For example, it has been known that chondroitin sulfate and dermatan sulfate, which are a kind of glycosaminoglycan, exist in a cell surface or an extracellular matrix as side chains of proteoglycan, and form various functional domains depending on the difference in sequences of sulfated disaccharide units to exhibit a variety of physiological functions. It is conceived that the sulfated saccharides have a high affinity with many cytokines and growth factors, which show various physiological activities in vivo even in minute amounts, and act to localize such factors to promote the various physiological effects.

Heretofore, as a method of producing such a sulfated saccharide, a method of collecting it from a natural product such as shark cartilage, a method of using a sulfating reagent (Patent Literature 1 to 4), a method of using an enzyme (Patent Literature 5 to 7), a method using chemical synthesis (Patent Literature 8 and 9), and the like have been developed. However, any of these methods is not necessarily adequate in terms of uniformity of the structure of a sulfated saccharide to be produced, production efficiency, or the like.

For example, when a sulfated saccharide is collected from a natural product, it is considered that the structure of the obtained sulfated saccharide is generally not uniform, and that the control of contaminants mixed therein is difficult. The method using a sulfating reagent exhibits low reactivity, and efficient sulfation is difficult.

A drawback of the method using an enzyme is that the position for introducing a sulfate group or a substrate to be used is limited, and the like, and also an enzyme to be used is expensive. Therefore, it is not an economical method. Further, in the case of preparing a sulfated saccharide by chemical synthesis from a saccharide having a sulfate group, protection of the sulfate group is necessary, while protection and deprotection of a sulfate group are difficult. In particular, as a saccharide of interest is a higher polymer, deprotection of the sulfate group becomes more difficult.

CITATION LIST

Patent Literature

[Patent Literature 1] Japanese Patent Laid-Open No. 2008-007643
[Patent Literature 2] Japanese Patent Laid-Open No. 2007-332226
[Patent Literature 3] Japanese Patent Laid-Open No. 2005-232064
[Patent Literature 4] Japanese Patent Laid-Open No. 06-065273
[Patent Literature 5] Re-publication of PCT International Publication No. 02/103025
[Patent Literature 6] Japanese Patent Laid-Open No. 2001-019698
[Patent Literature 7] Japanese Patent Laid-Open No. 09-263595
[Patent Literature 8] Japanese Patent Laid-Open No. 2014-047155
[Patent Literature 9] Re-publication of PCT International Publication No. 2013/141350

SUMMARY OF INVENTION

Technical Problem

An object of the present invention is to provide a method of efficiently producing a saccharide having a sulfate group and/or a phosphate group in the molecule, or a compound including the saccharide.

Another object of the present invention is to provide a method of efficiently producing a saccharide with a uniform structure having a sulfate group and/or a phosphate group in the molecule.

In particular, an object of the present invention is to provide a method capable of efficiently producing a long-chain compound comprising a saccharide having a sulfate group and/or a phosphate group, which has heretofore been considered to be difficult to synthesize.

Solution to Problem

The inventors of the present application diligently studied to achieve the objects. In the conventional method using chemical synthesis, a saccharide donor and a saccharide acceptor having a sulfate group at a desired position are prepared, and used for synthesis. Therefore, the method is capable of controlling the structure of a sulfated saccharide to be produced, and thus effective in producing a sulfated saccharide with a uniform structure. However, when a saccharide having a sulfate group in at least either of a saccharide donor or a saccharide acceptor is used in chemical synthesis for condensation (glycosylation), it has been considered that protection of the sulfate group is necessary. This has complicated the conventional method and placed restrictions on the variation of production routes for a compound containing a sulfated saccharide, and producible compounds. Therefore, it has been practically impossible to produce a compound containing a long-chain sulfated saccharide having a controlled structure. Further, a protected sulfate group has an electron withdrawing property, and thus also has a function as a leaving group, which is problematic in that a usable protecting group and a reaction route are restricted.

Under such a situation, the inventors of the present application have ventured to perform a condensation reaction using a saccharide having a non-protected sulfate group in the molecule, and as a result, they have found surprisingly that a sulfated saccharide having a controlled structure, or a compound containing the same can be produced, even if a sulfate group without protection is used for the reaction, thereby completed the present invention.

Compared to the conventional method using a protected sulfate group, the production method of the present invention dramatically increases usable protecting groups and reaction routes, because the sulfate group has no function as a leaving group. Consequently, a sulfated saccharide or a compound containing the same may be produced more easily and efficiently than before, and a type of sulfated saccharide, which has heretofore been difficult to synthesize, or a compound containing the same, can be now synthesized. The production method of the present invention is also useful for synthesizing a long-chain (for example, 10 saccharides to 100 saccharides) sulfated saccharide with a uniform structure, or a compound containing the same.

In addition to a method of preparing a saccharide having a sulfate group, the present invention may directly be applicable to a method of preparing a saccharide having a phosphate group from a saccharide donor or a saccharide acceptor having a non-protected phosphate group.

Accordingly, the present invention provides, in one aspect, a method of producing a saccharide having a sulfate group and/or a phosphate group. The production method is, in one embodiment, characterized by comprising the following steps:

(a) a step of preparing a "first saccharide having a non-protected sulfate group and/or a non-protected phosphate group" and a "second saccharide having a non-protected sulfate group and/or a non-protected phosphate group" and (b) a step of condensing the first saccharide and the second saccharide prepared in the step (a) with each other.

Further, in one embodiment of the present invention, the first saccharide and the second saccharide are characterized by each being a saccharide having a leaving group at a 1-position carbon atom of the saccharide and having a nucleophilic group.

Further, in one embodiment of the present invention, the first saccharide and the second saccharide are characterized by being the same saccharide.

Further, in one embodiment of the present invention, the nucleophilic group is characterized by being selected from a hydroxy group, an amino group, and a thiol group.

Further, in one embodiment of the present invention, the first saccharide and the second saccharide are characterized by each being a saccharide constituting a 6-membered ring, and having a leaving group at a 1-position carbon atom of the saccharide, having a nucleophilic group at least at any of positions 2, 3, 4, or 6 of the saccharide, and having at least one non-protected sulfate group at least at any of positions 2, 3, 4, or 6 of the saccharide.

Further, in one embodiment of the present invention, the first saccharide and the second saccharide are characterized by each being a saccharide constituting a 6-membered ring, and having a leaving group at a 1-position carbon atom of the saccharide, having a nucleophilic group at least at any of position 3 or 4 of the saccharide, and having a non-protected sulfate group at least at any of positions 2, 4, or 6 of the saccharide.

Further, in one embodiment of the present invention, the first saccharide and the second saccharide are characterized by being represented by the following formula:

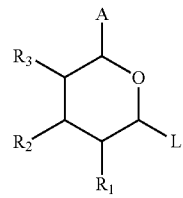

[Formula 1]

wherein
L is a leaving group;
A is selected from the group consisting of a hydrogen atom, a protected or non-protected carboxyl group, a protected or non-protected amide group, and —CH$_2$—R$_4$;
R$_1$ to R$_4$ are each independently selected from the group consisting of a hydrogen atom, a non-protected sulfate group, a non-protected phosphate group, a protected or non-protected hydroxy group, a protected or non-protected amino group, a protected or non-protected thiol group, and a saccharide residue;
at least one of R$_1$ to R$_4$ is a non-protected sulfate group or a non-protected phosphate group; and
at least one of R$_1$ to R$_4$ is a nucleophilic group selected from a hydroxy group, an amino group, and a thiol group.

Further, in one embodiment of the present invention, it is characterized in that in the above formula,
A is —CH$_2$—R$_4$;
R$_2$ to R$_4$ are selected from a non-protected sulfate group, a non-protected phosphate group, a protected or non-protected hydroxy group, and a saccharide residue,
provided that at least one of R$_2$ to R$_4$ is a non-protected sulfate group or a non-protected phosphate group; and
R$_1$ is a protected or non-protected amino group.

Further, in one embodiment of the present invention, the saccharide residue is characterized by being a glucuronic acid residue. In another embodiment of the present invention, the saccharide residue is characterized by being a glucuronic acid residue having a sulfate group at a 2-position carbon atom of the saccharide.

Further, in another embodiment of the present invention, the first saccharide and the second saccharide are characterized by being represented by the following formula:

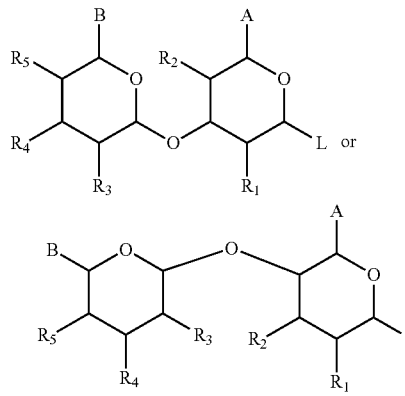

[Formula 2]

wherein
L is a leaving group;
A and B are each independently selected from the group consisting of a hydrogen atom, a protected or non-protected carboxyl group, a protected or non-protected amide group, and —CH$_2$—R$_6$;

$R_1$ to $R_6$ are each independently selected from the group consisting of a hydrogen atom, a non-protected sulfate group, a non-protected phosphate group, a protected or non-protected hydroxy group, a protected or non-protected amino group, a protected or non-protected thiol group, and a saccharide residue;

at least one of $R_1$ to $R_6$ is a non-protected sulfate group or a non-protected phosphate group; and at least one of $R_1$ to $R_6$ is a nucleophilic group selected from a hydroxy group, an amino group, and a thiol group.

Further, in one embodiment of the present invention, it is characterized in that in the above formula, A is —$CH_2$—$R_6$; and B is a protected or non-protected carboxyl group;

$R_2$ to $R_6$ are each independently selected from a non-protected sulfate group, a non-protected phosphate group, and a protected or non-protected hydroxy group, and a saccharide residue, provided that at least one of $R_2$ to $R_6$ is a non-protected sulfate group or a non-protected phosphate group; and $R_1$ is a protected or non-protected amino group.

Further, in one embodiment of the present invention, production method of the present invention is characterized by being a method of producing a polysaccharide of 2 sugars(disaccharide) to 100 sugars(hectosaccharide).

Further, in one embodiment of the present invention, the production method of the present invention is characterized by being a method of producing chondroitin sulfate or heparan sulfate.

In another aspect, the present invention relates to a method of producing a compound comprising a saccharide having a sulfate group and/or a phosphate group. The production method is characterized by comprising the following steps:

(a1) a step of preparing a "first saccharide having a non-protected sulfate group and/or a non-protected phosphate group" and (b1) a step of condensing the first saccharide prepared in the step (a1) with a "compound having a nucleophilic group".

Further, in one embodiment of the present invention, the first saccharide is characterized by being a saccharide having a leaving group at position 1 of the saccharide.

Further, in one embodiment of the present invention, the method is characterized by comprising (c1) a step of further condensing the "compound comprising a saccharide having a sulfate group and/or a phosphate group" prepared in the step (b1) with a compound selected from a "saccharide having a non-protected sulfate group and/or a non-protected phosphate group", a "compound having a nucleophilic group", and the "compound comprising a saccharide having a sulfate group and/or a phosphate group" prepared in the step (b1).

Further, in one embodiment of the present invention, the nucleophilic group is characterized by being selected from a hydroxy group, an amino group, and a thiol group. Further, in one embodiment of the present invention, the compound having a nucleophilic group is characterized by being selected from a saccharide, an amino acid, a peptide, a protein, and a derivative thereof.

Further, in one embodiment of the present invention, the "saccharide having a non-protected sulfate group and/or a non-protected phosphate group" is characterized by being a saccharide constituting a 6-membered ring, and having a leaving group at a 1-position carbon atom of the saccharide, having a nucleophilic group at least at any of positions 2, 3, 4, or 6 of the saccharide, and having at least one non-protected sulfate group at least at any of positions 2, 3, 4, or 6 of the saccharide.

Further, in one embodiment of the present invention, the first saccharide is characterized by being a saccharide constituting a 6-membered ring, and having a leaving group at a 1-position carbon atom of the saccharide, having a nucleophilic group at least at any of position 3 or 4 of the saccharide, and having a non-protected sulfate group at least at any of positions 2, 4, or 6 of the saccharide.

Further, in one embodiment of the present invention, the first saccharide is characterized by being a compound having a structure represented by the following formula:

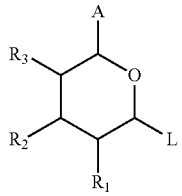

[Formula 3]

wherein

L is a leaving group;

A is selected from the group consisting of a hydrogen atom, a protected or non-protected carboxyl group, a protected or non-protected amide group, and —$CH_2$—$R_4$;

$R_1$ to $R_4$ are each independently selected from the group consisting of a hydrogen atom, a non-protected sulfate group, a non-protected phosphate group, a protected or non-protected hydroxy group, a protected or non-protected amino group, a protected or non-protected thiol group, and a saccharide residue;

at least one of $R_1$ to $R_4$ is a non-protected sulfate group or a non-protected phosphate group; and at least one of $R_1$ to $R_4$ has a nucleophilic group selected from a hydroxy group, an amino group, and a thiol group.

Further, in one embodiment of the present invention, it is characterized in that in the above formula, A is —$CH_2$—$R_4$;

$R_3$ is selected from a non-protected sulfate group, a non-protected phosphate group, a protected or non-protected hydroxy group, and a saccharide residue;

$R_4$ is selected from a non-protected sulfate group, a non-protected phosphate group, and a protected or non-protected hydroxy group, provided that at least one of $R_4$ and $R_3$ is a non-protected sulfate group or a non-protected phosphate group;

$R_1$ is a protected or non-protected amino group; and $R_2$ is a non-protected hydroxy group or a saccharide residue.

Those skilled in the art will appreciate that any invention optionally combining one or more of the features of the present invention described above is also within the scope of the present invention.

Advantageous Effects of Invention

According to the production method of the present invention, a saccharide having a sulfate group and/or a phosphate group, or a compound containing the saccharide can be efficiently produced.

Further, according to the production method of the present invention, a saccharide with a uniform structure having a sulfate group and/or a phosphate group in the molecule can be efficiently produced.

Further, according to the production method of the present invention, a compound containing a sulfated saccharide and/or a phosphorylated saccharide can be produced more easily and efficiently than before, because a reaction route for producing a saccharide having a sulfate group and/or a phosphate group, or a compound containing the saccharide, and a usable protecting group dramatically increase. The production method of the present invention is useful for synthesizing a sulfated saccharide and/or a phosphorylated saccharide having a long-chain uniform structure, or a compound containing the same, which have heretofore been considered to be difficult to produce.

DESCRIPTION OF EMBODIMENTS

A "saccharide" or a "saccharide residue" means herein a compound composed of one or more unit saccharides (monosaccharides and/or derivatives thereof) linked in the form of a chain (also referred to herein as "saccharide chain"). When two or more unit saccharides are linked, the unit saccharides are bonded by dehydration condensation through a glycosidic linkage therebetween. Examples of such a saccharide chain include as broad as a monosaccharide and a polysaccharide contained in living organisms (glucose, galactose, mannose, fucose, xylose, N-acetylglucosamine, N-acetylgalactosamine, sialic acid, and a complex or a derivative thereof), as well as a degraded polysaccharide, and a saccharide chain degraded or derived from a complex biomolecule, such as glycoprotein, proteoglycan, glycosaminoglycan, and glycolipid, but not limited thereto. The saccharide chain may be linear or branched.

Further, a "saccharide" or a "saccharide residue" includes herein also a derivative of a saccharide. As the derivative of a saccharide, a saccharide in which a hydroxy group of any carbon atom of the saccharide is substituted with another substituent, or which is derivatized by bonding with a protecting group or another substituent is included. Examples thereof include saccharide chains in which a saccharide constituting the saccharide chain is a saccharide having a carboxyl group (such as aldonic acid whose C-1 position is oxidized to carboxylic acid (e.g. D-gluconic acid oxidized from D-glucose), or uronic acid in which a terminal C atom is changed to carboxylic acid (e.g. D-glucuronic acid oxidized from D-glucose)), a saccharide having an amino group or a derivative of an amino group (e.g. an acetylated amino group) (such as N-acetyl-D-glucosamine and N-acetyl-D-galactosamine), a saccharide having both an amino group and a carboxyl group (such as N-acetylneuramic acid (sialic acid) and N-acetylmuramic acid), a deoxidized saccharide (such as 2-deoxy-D-ribose), a sulfated saccharide containing a sulfate group, and a phosphorylated saccharide containing a phosphate group, but not limited thereto.

A saccharide containing a sulfate group is described herein also as a "sulfated saccharide", and a saccharide containing a phosphate group is described also as a "phosphorylated saccharide". Further, a saccharide having both a sulfate group and a phosphate group is described also as a "sulfated/phosphorylated saccharide".

In the present invention, the "uniform structure" used particularly for a sulfated saccharide, a phosphorylated saccharide and a sulfated/phosphorylated saccharide as targets to be produced, means that the position and number of sulfate groups, the type of constituent saccharide, and the type of a linkage between the saccharides in a saccharide skeleton, which is a constituent unit for the saccharide or a compound to be condensed (or polymerized), are equal.

It should be noted that, in a case where a "saccharide", a "saccharide residue", and an "amino acid" are described herein without discrimination between D-isomer and L-isomer, it is understood that any stereoisomers are included.

The present invention will be described below in detail.

In one aspect, the present invention relates to a method of producing a saccharide having a sulfate group and/or a phosphate group, and the method is characterized by comprising the following steps:

(a) a step of preparing a "first saccharide having a non-protected sulfate group and/or a non-protected phosphate group" and a "second saccharide having a non-protected sulfate group and/or a non-protected phosphate group" and (b) a step of condensing the first saccharide and the second saccharide prepared in the step (a) with each other.

A "saccharide having a non-protected sulfate group and/or a non-protected phosphate group" to be used as a raw material in the production method of the present invention refers to herein an optional saccharide having at least one sulfated hydroxy group ($-O-SO_3H$, $-O-SO_3-$, $-O-SO_3Na$, or $-O-SO_3$ metal), or a phosphorylated hydroxy group ($-O-PO_3H_2$ or $-O-PO_3^{2-}$) in the absence of a protecting group as a substituent at an optional carbon atom. It should be noted that, a "sulfate group" and a "sulfated hydroxy group", and a "phosphate group" and a "phosphorylated hydroxy group" are used herein interchangeably.

In the method of the present invention, the first saccharide and the second saccharide are defined such that either one functions as a saccharide donor and the other one functions as a saccharide acceptor. In this regard, the first saccharide may function as a saccharide donor, and the second saccharide may function as a saccharide acceptor, or vice versa. In addition, the first saccharide and the second saccharide may each be a monosaccharide, or have a saccharide skeleton of disaccharide, trisaccharide, tetrasaccharide, or more.

The function as a saccharide donor is retained if a saccharide has a leaving group at any carbon atom position. In a specific embodiment of the present invention, "(the first or the second) saccharide having a non-protected sulfate group and/or a non-protected phosphate group" functioning as a saccharide donor is a saccharide having a leaving group at the position of a 1-position carbon atom. In the embodiment, when the saccharide functioning as a saccharide donor has a saccharide skeleton having two or more saccharides, the saccharide donor has a leaving group at the position of a 1-position carbon atom of the reducing terminal.

On the other hand, the function as a saccharide acceptor is retained if a saccharide has a nucleophilic group at any carbon atom position. The term "nucleophilic" as used in the present invention refers to a nature to react easily with a cationic element of a Lewis acid. In the present invention, there is no particular restriction on the nucleophilic group, insofar as it is a functional group having such a nature. In the present invention, the nucleophilic group is particularly a functional group selected from a hydroxy group, an amino group, or a thiol group.

In one embodiment of the present invention, a "(first or second) saccharide having a non-protected sulfate group and/or a non-protected phosphate group" may have both a function as saccharide donor and a function as saccharide acceptor. In this case, the "(first or second) saccharide having a non-protected sulfate group and/or a non-protected phosphate group" has both a leaving group and a nucleophilic group. In one embodiment of the present invention, a "(first or second) saccharide having a non-protected sulfate group and/or a non-protected phosphate group" is a saccharide having a leaving group at the position of a 1-position carbon atom and having a nucleophilic group.

In the present invention, the first saccharide and the second saccharide may be the same saccharide or different saccharides.

In a preferable embodiment of the present invention, the first saccharide and the second saccharide each have the following properties:
constituting a 6-membered ring;
having a leaving group at a 1-position carbon atom of the saccharide;
having a nucleophilic group at least at any of positions 2, 3, 4, or 6 of the saccharide; and
having at least one non-protected sulfate group or non-protected phosphate group at least at any of positions 2, 3, 4, or 6 of the saccharide.

Preferably, the first saccharide and the second saccharide have a nucleophilic group at any of position 3 or 4 of the saccharide, and/or a non-protected sulfate group or a non-protected phosphate group at least at any of positions 2, 4, or 6 of the saccharide.

In a further preferable embodiment of the present invention, the first saccharide and the second saccharide are each a saccharide represented by the following formula:

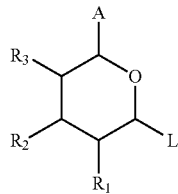

[Formula 4]

wherein
L is a leaving group;
A is selected from the group consisting of a hydrogen atom, a protected or non-protected carboxyl group, a protected or non-protected amide group, and —$CH_2$—$R_4$;
$R_1$ to $R_4$ are each independently selected from the group consisting of a hydrogen atom, a non-protected sulfate group, a non-protected phosphate group, a protected or non-protected hydroxy group, a protected or non-protected amino group, a protected or non-protected thiol group, and a saccharide residue;
at least one of $R_1$ to $R_4$ is a non-protected sulfate group or a non-protected phosphate group; and
at least one of $R_1$ to $R_4$ is a nucleophilic group selected from a hydroxy group, an amino group, and a thiol group.

In a preferable embodiment, A is —$CH_2$—$R_4$, one of $R_3$ and $R_4$ is a non-protected sulfate group or a non-protected phosphate group. In another preferable embodiment, A is —$CH_2$—$R_4$, and both $R_3$ and $R_4$ are a non-protected sulfate group or a non-protected phosphate group.

In a preferable embodiment, $R_1$ in the formula is a protected or non-protected amino group.

In a preferable embodiment, $R_2$ in the formula is a non-protected hydroxy group or a saccharide residue.

In an especially preferable embodiment, in the above formula:
A is —$CH_2$—$R_4$;
$R_3$ is selected from a non-protected sulfate group, a non-protected phosphate group, a protected or non-protected hydroxy group, and a saccharide residue;
$R_a$ is selected from a non-protected sulfate group, a non-protected phosphate group, and a protected or non-protected hydroxy group,
provided that at least one of $R_4$ and $R_3$ is a non-protected sulfate group or a non-protected phosphate group;
$R_1$ is a protected or non-protected amino group; and
$R_2$ is a non-protected hydroxy group or a saccharide residue.

Examples of such a saccharide include, but not limited to, glucosamine and galactosamine, having a non-protected sulfate group and/or a non-protected phosphate group, as well as a compound in which an optional saccharide residue is bonded to any of glucosamine and galactosamine.

In an especially preferable embodiment of the present invention, $R_2$ is a glucuronic acid residue. Examples of such a saccharide include, but not limited to, a disaccharide, which is a constituent unit of a glycosaminoglycan selected from chondroitin-4-sulfate (chondroitin sulfate A), chondroitin-6-sulfate (chondroitin sulfate C), dermatan sulfate (chondroitin sulfate B), and a heparan sulfate.

In another preferable embodiment of the present invention, $R_2$ is a glucuronic acid residue having a sulfate group at a 2-position carbon atom of a saccharide. Examples of such a saccharide include, but not limited to, a disaccharide, which is a constituent unit of glycosaminoglycan such as chondroitin sulfate D.

In a further preferable embodiment of the present invention, the first saccharide and the second saccharide are the same saccharide.

In another preferable embodiment of the present invention, the first saccharide and the second saccharide are each a saccharide represented by the following formula:

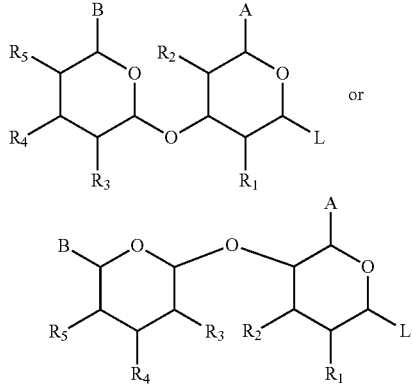

[Formula 5]

wherein
L is a leaving group;
A and B are each independently selected from the group consisting of a hydrogen atom, a protected or non-protected carboxyl group, a protected or non-protected amide group, and —$CH_2$—$R_6$;
$R_1$ to $R_6$ are each independently selected from the group consisting of a hydrogen atom, a non-protected sulfate group, a non-protected phosphate group, a protected or non-protected hydroxy group, a protected or non-protected amino group, a protected or non-protected thiol group, and a saccharide residue;

at least one of $R_1$ to $R_6$ is a non-protected sulfate group or a non-protected phosphate group; and at least one of $R_1$ to $R_6$ is a nucleophilic group selected from a hydroxy group, an amino group, and a thiol group.

In the above embodiment, when both A and B are —$CH_2$—$R_6$, the $R_6$ in A and the $R_6$ in B may be the same or different from each other.

In a preferable embodiment, A is —$CH_2$—$R_6$, and/or B is a protected or non-protected carboxyl group. Preferably, A is —$CH_2$—$R_6$, and any one or two of $R_2$, $R_3$, and $R_6$ are a non-protected sulfate group or a non-protected phosphate group. Preferably, $R_4$ and $R_5$ are a protected or non-protected hydroxy group.

In another preferable embodiment, A is a protected or non-protected carboxyl group, and/or B is —$CH_2$—$R_6$. Preferably, B is —$CH_2$—$R_6$, and any one or two of $R_1$, $R_5$ and $R_6$ are a non-protected sulfate group or a non-protected phosphate group. Preferably, $R_4$ or $R_5$ is a protected or non-protected hydroxy group.

In another preferable embodiment, in the above formula:
A is —$CH_2$—$R_6$;
B is a protected or non-protected carboxyl group;
$R_2$ to $R_6$ are each independently selected from a non-protected sulfate group, a non-protected phosphate group, and a protected or non-protected hydroxy group, as well as a saccharide residue, provided that at least one of $R_2$ to $R_6$ is a non-protected sulfate group or a non-protected phosphate group; and
$R_1$ is a protected or non-protected amino group.

In another preferable embodiment, in the above formula:
A is a protected or non-protected carboxyl group;
B is —$CH_2$—$R_6$;
$R_2$ to $R_6$ are each independently selected from a non-protected sulfate group, a non-protected phosphate group, and a protected or non-protected hydroxy group, as well as a saccharide residue, provided that at least one of $R_2$ to $R_6$ is a non-protected sulfate group or a non-protected phosphate group; and
$R_3$ is a protected or non-protected amino group.

In an especially preferable embodiment, in the above formula:
A is —$CH_2$—$R_6$;
B is a protected or non-protected carboxyl group;
any one or two of $R_2$, $R_3$, and $R_6$ are a non-protected sulfate group or a non-protected phosphate group;
$R_4$ and $R_5$ are a protected or non-protected hydroxy group; and
$R_1$ is a protected or non-protected amino group.

In especially preferable another embodiment, in the above formula:
A is a protected or non-protected carboxyl group;
B is —$CH_2$—$R_6$;
any one or two of $R_1$, $R_5$, and $R_6$ are a non-protected sulfate group or a non-protected phosphate group;
$R_4$ or $R_5$ is a protected or non-protected hydroxy group; and
$R_3$ is a protected or non-protected amino group.

Examples of the above saccharide include, but not limited to, a disaccharide, which is a constituent unit of a glycosaminoglycan selected from chondroitin-4-sulfate (chondroitin sulfate A), chondroitin-6-sulfate (chondroitin sulfate C), dermatan sulfate (chondroitin sulfate B), chondroitin sulfate D, and a heparan sulfate.

The production method of the present invention can comprise a step (c) of further condensing a saccharide condensed in the step (b) with a third saccharide. The "third saccharide" may be used as a saccharide donor, or as a saccharide acceptor, and may be the same saccharide as the saccharide condensed in the step (b), or a different saccharide.

In a case where neither the "saccharide condensed in the step (b)" nor the "third saccharide" has a leaving group, a treatment for introducing a leaving group into either of the saccharides can be performed for further condensation.

In a preferable embodiment, the step (c) is carried out multiple times. By performing the step (c) multiple times, a saccharide with a desired length can be prepared, while controlling the structure.

In a case where the production method of the present invention comprises the step (c) performed once or multiple times, the step (b) and the step (c) performed once or multiple times, may be performed at the same time or at different times. When the step (b) and the step (c) performed multiple times are performed at the same time, a saccharide having a leaving group at the position of a 1-position carbon atom at its reducing terminal and having a nucleophilic group is preferably used as the "first saccharide", the "second saccharide", and the "third saccharide" for enabling continuous condensation (polymerization). In this embodiment, from the viewpoint of producing a saccharide having a controlled structure, it is more preferable to use the same saccharide having a non-protected sulfate group and/or a non-protected phosphate group for the "first saccharide", the "second saccharide", and the "third saccharide". For example, a uniform population of monosaccharides with the same structure, having a non-protected sulfate group and/or a non-protected phosphate group, a leaving group, and a nucleophilic group, respectively at the same positions is prepared, and the monosaccharides are each condensed (polymerized), so that a long-chain saccharide having a controlled structure can be produced.

In an exemplary embodiment, the production method of the present invention is a method, by which, as a saccharide for the "first saccharide", the "second saccharide", and the "third saccharide", a uniform population composed of a disaccharide skeleton, which is a constituent unit of chondroitin A, chondroitin C, chondroitin D, chondroitin E, or heparan sulfate, is prepared and condensed (polymerized) to produce chondroitin sulfate or heparan sulfate represented by the following formula.

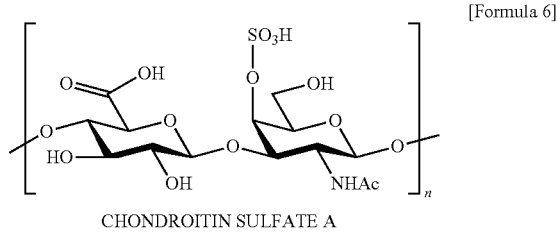

CHONDROITIN SULFATE A

[Formula 6]

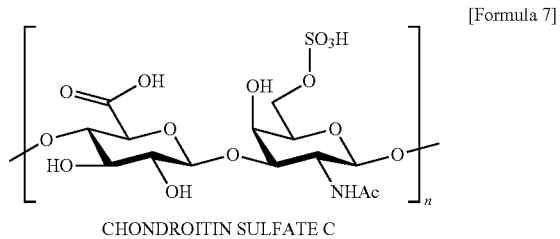

CHONDROITIN SULFATE C

[Formula 7]

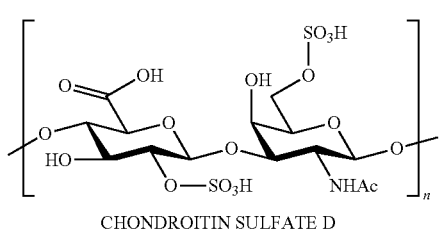

CHONDROITIN SULFATE D [Formula 8]

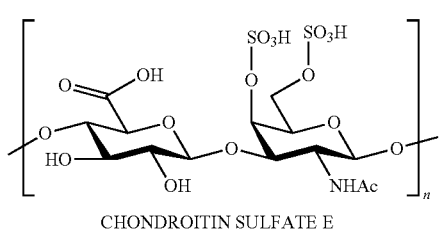

CHONDROITIN SULFATE E [Formula 9]

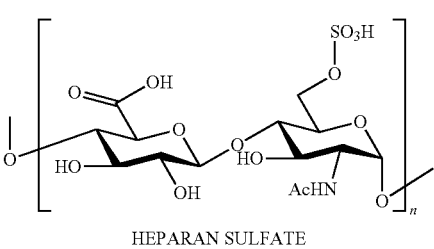

HEPARAN SULFATE [Formula 10]

In the disaccharide skeleton shown above, which is a constituent unit of chondroitin A, chondroitin C, chondroitin D, chondroitin E, or heparan sulfate, it is needless to say that the positions of the aminosaccharide and the uronic acid constituting the disaccharide skeleton may be reversed.

By way of example, it is naturally contemplated that the production method of the present invention includes the method of producing heparan sulfate shown below.

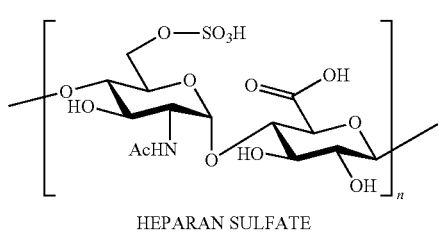

HEPARAN SULFATE [Formula 11]

In the above formula, n is 1 to 50, preferably 1 to 25, and more preferably 1 to 10.

Therefore, in one embodiment, the production method of the present invention is a method of producing a sulfated saccharide, a phosphorylated saccharide, or a sulfated/phosphorylated saccharide containing 2 saccharides to 100 saccharides, preferably 2 saccharides to 50 saccharides, and more preferably 2 saccharides to 20 saccharides.

In another aspect, the production method of the present invention relates to a method of producing a compound comprising a saccharide having a sulfate group and/or a phosphate group. In this aspect, a "compound having a nucleophilic group" is used in place of the "second saccharide" and condensed with the "first saccharide".

Therefore, in this aspect, the production method of the present invention is characterized by comprising:

(a1) a step of preparing a "saccharide having a non-protected sulfate group and/or a non-protected phosphate group" and (b1) a step of condensing the "saccharide having a non-protected sulfate group and/or a non-protected phosphate group" prepared in the step (a1) and a "compound having a nucleophilic group".

In this aspect, the "saccharide having a non-protected sulfate group and/or a non-protected phosphate group" is used as a saccharide donor for a "compound having a nucleophilic group". Therefore, the "saccharide having a non-protected sulfate group and/or a non-protected phosphate group" is a saccharide having a leaving group and is typically a saccharide having a leaving group at the position of a 1-position carbon atom of the saccharide.

A "nucleophilic group" of a "compound having a nucleophilic group" is the same as defined above and refers to any functional group having a nature to react easily with a cationic element of a Lewis acid. In one embodiment, such a functional group is selected from a hydroxy group, an amino group, and a thiol group. There is no particular restriction on a "compound having a nucleophilic group", insofar as it is a compound having a nucleophilic group, and includes, for example, besides saccharides, an amino acid, a peptide, and a protein.

In the present invention, the "amino acid" is used in its broadest sense and includes not only natural amino acids, such as serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gln), threonine (Thr), cysteine (Cys), methionine (Met), phenylalanine (Phe), tryptophan (Trp), and proline (Pro); but also non-natural amino acids, such as an amino acid variant and derivative. In view of the broad definition, those skilled in the art will appreciate that amino acids in the present invention include, for example, an L-amino acid; a D-amino acid; a chemically modified amino acid, such as an amino acid variant and derivative; an amino acid that cannot be a material constituting a protein in vivo, such as norleucine, β-alanine, and ornithine; and a chemically synthesized compound that has the properties of an amino acid known to those skilled in the art.

An amino acid derivative includes herein a compound in which a side-chain substituent of an amino acid is further substituted with another substituent, and a compound derivatized by bonding a protecting group or another substituent to a functional group, such as an amino group and a carboxyl group. In other words, the amino acid derivative is used herein for generally expressing amino acids including those derivatized as these examples, but not aim to exclude an amino acid not derivatized.

A derivative of a peptide or a protein includes herein besides a peptide or a protein including an amino acid derivative; also a hydrolysis product of a protein obtained by partial hydrolysis of a peptide or a protein with an acid, an alkali, or an enzyme; and a derivative thereof, such as a cationized product, an acylated product, an alkyl esterified product, and a siliconized product.

In an exemplary embodiment of the present invention, the number of molecules constituting a "compound comprising a saccharide having a sulfate group and/or a phosphate group" prepared in the step (b1) may be 2, 3, 4, 5 or more.

In a preferable embodiment, the production method of the present invention comprises (c1) a step of further condensing a "compound comprising a saccharide having a sulfate group and/or a phosphate group" prepared in the step (b1)

with a compound selected from a "saccharide having a non-protected sulfate group and/or a non-protected phosphate group", a "compound having a nucleophilic group", and a "compound comprising a saccharide having a sulfate group and/or a phosphate group" prepared in the step (b1). In this embodiment, the sulfate group and/or the phosphate group in the "compound comprising a saccharide having a sulfate group and/or a phosphate group" subjected to further condensation is non-protected.

In a case where the step (c1) is a step of condensing a "compound comprising a saccharide having a sulfate group and/or a phosphate group" prepared in the step (b1) with a "saccharide having a non-protected sulfate group and/or a non-protected phosphate group", the "compound comprising a saccharide having a sulfate group and/or a phosphate group" may be used as a saccharide donor or as a saccharide acceptor. In a case where neither the "compound comprising a saccharide having a sulfate group and/or a phosphate group" nor the "saccharide having a non-protected sulfate group and/or a non-protected phosphate group" has a leaving group, a treatment for introducing a leaving group can be performed on either of them for further condensation.

In a case where the step (c1) is a step of condensing a "compound comprising a saccharide having a sulfate group and/or a phosphate group" prepared in the step (b1) with a "compound having a nucleophilic group", the "compound comprising a saccharide having a sulfate group and/or a phosphate group" can be used as a saccharide donor. In a case where the "compound comprising a saccharide having a sulfate group and/or a phosphate group" does not have a leaving group, a treatment for introducing a leaving group can be performed for further condensation.

In a case where the step (c1) is a step of condensing a "compound comprising a saccharide having a sulfate group and/or a phosphate group" prepared in the step (b1) with a "compound comprising a saccharide having a sulfate group and/or a phosphate group" prepared in the step (b1), a compound having a leaving group as well as a nucleophilic group is used as the "compound comprising a saccharide having a sulfate group and/or a phosphate group". In a case where the "compound comprising a saccharide having a sulfate group and/or a phosphate group" does not have a leaving group, a treatment for introducing a leaving group can be performed for further condensation.

In a preferable embodiment, the step (c1) is performed multiple times. By performing the step (c1) multiple times, a desired length of compound having the controlled structure can be prepared. The step (c1) may be performed multiple times at the same time or at different times.

In a case where the step (c1) is performed multiple times at the same time in the production method of the present invention, the step (c1) is preferably a step of condensing a "compound comprising a saccharide having a sulfate group and/or a phosphate group" prepared in the step (b1) with a "compound comprising a saccharide having a sulfate group and/or a phosphate group" prepared in the step (b1) from the viewpoint of producing a compound having a controlled structure. For example, a uniform population of compounds with the same structure, having a non-protected sulfate group and/or a non-protected phosphate group, a leaving group, and a nucleophilic group, respectively at the same positions is prepared, and the compounds are each condensed (polymerized), so that a long-chain compound having a controlled structure can be produced.

In an exemplary embodiment of the present invention, the "compound comprising a saccharide having a sulfate group and/or a phosphate group" prepared in the step (b1) is a disaccharide, a tetrasaccharide, a hexasaccharide, an octasaccharide, a decasaccharide, or a higher saccharide.

In other exemplary embodiments of the present invention, the "compound comprising a saccharide having a sulfate group and/or a phosphate group" prepared in the step (b1) is a disaccharide skeleton, which is a constituent unit for chondroitin A, chondroitin C, chondroitin D, chondroitin E, or heparan sulfate.

In an exemplary embodiment of the present invention, the "compound comprising a saccharide having a sulfate group and/or a phosphate group" prepared in the step (b1) is a compound containing a sulfated saccharide, a phosphorylated saccharide, or a sulfated/phosphorylated saccharide, having a bimolecular skeleton, and in the step (c1), based on the bimolecular skeleton as a condensation or polymerization unit, a compound with a length of 4 molecules, 6 molecules, 8 molecules, 10 molecules, or more is produced.

In other exemplary embodiments of the present invention, the "compound comprising a saccharide having a sulfate group and/or a phosphate group" prepared in the step (b1) is a disaccharide, which is a constituent unit for chondroitin A, chondroitin C, chondroitin D, chondroitin E, or heparan sulfate, a tetrasaccharide, a hexasaccharide, an octasaccharide, a decasaccharide, or a higher saccharide, and in the step (c1), based on these saccharides as a condensation or polymerization unit, a longer-chain glycosaminoglycan is produced.

In other exemplary embodiments of the present invention, the "compound comprising a saccharide having a sulfate group and/or a phosphate group" prepared in the step (b1) is a disaccharide, which is a constituent unit for chondroitin A, chondroitin C, chondroitin D, chondroitin E, or heparan sulfate, and in the step (c1), based on the disaccharide as a condensation or polymerization unit, a glycosaminoglycan with a length of tetrasaccharide, hexasaccharide, octasaccharide, decasaccharide, or more is produced.

A "saccharide having a non-protected sulfate group" which is a raw material of the present invention can be prepared by any method known to those skilled in the art. For example, but not limited to, it can be prepared by making a sulfating agent act on a given saccharide having a non-protected hydroxy group. Specifically, a saccharide in which a hydroxy group is sulfated can be synthesized by making a sulfating agent react with a given saccharide having a non-protected hydroxy group as a raw material, in a proper solvent, such as DMF in the conditions of a proper equivalent (1 to 100 equivalents), a proper reaction temperature (0 to 100° C.), and a reaction time (10 min to 2 days).

Any sulfating agent may be used insofar as it is used for sulfating a saccharic compound, and examples thereof include a sulfur trioxide-pyridine complex, a sulfur trioxide-trimethylamine complex, a chlorosulfonic acid-pyridine complex, and dicyclohexyl carbodiimide-sulfuric acid. Preferable examples include a sulfur trioxide-pyridine complex and a sulfur trioxide-trimethylamine complex.

Methods of introducing a sulfate group into a selected position are also known to those skilled in the art. For example, a saccharide in which only a specific hydroxy group is sulfated can be prepared by selectively protecting a hydroxy group which is not to be sulfated prior to the reaction with a sulfating agent. In addition, by using an enzyme capable of introducing a sulfate group into a specific position of a saccharide, it is also possible to introduce a sulfate group into a specific position.

A "saccharide having a non-protected phosphate group", which is a raw material of the present invention, may be carried out generally in the same manner as sulfation. That is, it can be prepared by making a phosphorylating agent act on a given saccharide having a non-protected hydroxy group. Examples of a suitable phosphorylating agent include, but not limited to, phosphoric acid, polyphosphoric acid, phosphorus pentoxide, and $POCl_3$.

The obtained compound can be, if necessary, separated and purified by high performance thin layer chromatography using silica gel, etc., or high performance liquid chromatography using an amide column, etc.

In the present invention, a condensation reaction can be performed according to a method well-known to those skilled in the art. For example, in the present invention, a condensation reaction can be performed by using a method in which a saccharide donor and a saccharide acceptor are reacted in the presence of an acid.

Examples of an acid that can be used in the production method of the present invention include, but not limited to, an inorganic acid such as sulfuric acid, boron trifluoride diethyl ether (BF3-OEt2), dimethyl(methylthio)sulfonium trifluoromethanesulfonate (DMTST), trimethylsilyl trifluoromethanesulfonate, triethylsilyl trifluoromethanesulfonate, tripropylsilyl trifluoromethanesulfonate, dimethylethylsilyl trifluoromethanesulfonate, tribenzylsilyl trifluoromethanesulfonate, trinaphthylsilyl trifluoromethanesulfonate, or tribenzylmethylsilyl trifluoromethanesulfonate, silver trifluoromethanesulfonate, cyclopentadienyl hafnium chloride, cyclopentadienyl zirconium chloride, a Lewis acid such as tin chloride, and an organic acid, such as formic acid, acetic acid, trifluoroacetic acid, trifluoroacetic anhydride, trifluoromethanesulfonic acid, and tetrafluoromethanesulfonic acid.

These acids may be used singly or in combinations of two or more. The amount of the acid to be used may be 0.1 to 5 equivalents, for example 0.2 to 1.5 equivalents with respect to a saccharide donor. In a case where a saccharide or a compound used as a saccharide donor, and a saccharide or a compound used as a saccharide acceptor are compounds different from each other, the usage ratio of the saccharide donor to the saccharide acceptor may be any ratio. For example, the usage ratio of a saccharide acceptor may be 0.2 to 10 moles, and preferably 0.7 to 4 moles per mole of a saccharide donor.

In one embodiment of the present invention, an activator such as N-iodosuccinimide is used singly or in combination with a Lewis acid, such as tetrafluoromethanesulfonic acid and trimethylsilyl trifluoromethanesulfonate in a condensation reaction. When an activator is used in combination with a Lewis acid, the usage ratio may be, for example, with respect to a saccharide donor about 0.1 to 2 equivalents of a Lewis acid, and about 1 to 5 equivalents of an activator.

There is no restriction on a solvent used for a condensation reaction, insofar as it is a solvent inert to the reaction. Examples thereof include an aliphatic hydrocarbon, such as hexane, heptane, and pentane; an alicyclic hydrocarbon, such as cyclohexane; an aromatic hydrocarbon, such as benzene, toluene and xylene; a halogenated hydrocarbon, such as dichloromethane, chloroform, 1,2-dichloroethane, 1,1,1-trichloroethane, tetrachlorethylene, trichlorethylene, carbon tetrachloride, chlorobenzene, and o-dichlorobenzene; an ether, such as diethyl ether, isopropyl ether, tetrahydrofuran, dioxane, and Monoglyme; an amide, such as N,N-dimethylformamide, N,N-dimethylacetamide, and 1,3-dimethylimidazolidinone; a sulfoxide, such as dimethylsulfoxide; a nitrile, such as acetonitrile and propanenitrile; and a mixed solvent thereof.

A temperature used for the condensation reaction is in a range of −80° C. to 40° C., for example, −40° C. to 25° C.

In the production method of the present invention, as shown in the following Examples, the three-dimensional structure of a saccharide to be produced can be controlled by controlling the reaction temperature during the condensation reaction. Specifically, when the temperature during the condensation reaction is lower within the above-mentioned temperature range, a saccharide bound by a β-glycosidic linkage, or a compound containing the saccharide tends to be obtained, and when the temperature during the condensation reaction is higher within the above-mentioned temperature range, a saccharide bound by an α-glycosidic linkage, or a compound containing the saccharide tends to be obtained.

It is preferable to remove water, a hydrohalic acid, etc. in the system prior to the condensation reaction. For this purpose, for example, a trapping material such as a molecular sieve can be used.

A production method of the present invention can optionally comprise a step of introducing a leaving group into a "saccharide having a non-protected sulfate group and/or a non-protected phosphate group" or a "compound comprising a saccharide having a sulfate group and/or a phosphate group". The leaving group to be used in the present invention is not particularly limited, insofar as it has nucleophilicity lower than that of an atom or an atomic group to be replaced under the conditions for a condensation reaction between a saccharide donor and a saccharide acceptor, and ability to be eliminated.

Specific examples of a leaving group used in the present invention include, but not limited to, a halogen atom, a substituted or unsubstituted —O-alkyl group, a substituted or unsubstituted —O-alkenyl group, a substituted or unsubstituted —O-alkynyl group, a substituted or unsubstituted —O-aryl group, a substituted or unsubstituted —O-heteroaryl group, a substituted or unsubstituted —S-alkyl group, a substituted or unsubstituted —S-alkenyl group, a substituted or unsubstituted —S-alkynyl group, a substituted or unsubstituted —S-aryl group, and a substituted or unsubstituted —S-heteroaryl group.

Introduction of a leaving group can be performed according to a conventional method. For example, it can be performed by a halogenation reaction with a halogenating agent, or a reaction with a thiol compound in the presence of an acid or a base.

Examples of a halogenating agent that can be used in the present invention include chlorine, bromine, iodine, N-chlorosuccinimide, N-bromosuccinimide, and hydrogen bromide.

Examples of a solvent used in the halogenation reaction may include a halogenated hydrocarbon-based solvent, such as methylene chloride, 1,2-dichloroethane, chloroform, and carbon tetrachloride; an ether-based solvent, such as diethyl ether, tetrahydrofuran, and 1,4-dioxane; acetic acid, and water. These solvents may be used singly or a mixture of a plurality thereof may be used.

Examples of the thiol compound include methylthiol, isopropylthiol, thiophenol, and p-toluenethiol.

Examples of the acid include a Lewis acid, such as boron trifluoride diethyl ether (BF3-OEt2). Meanwhile, examples of the base include 1,3-dimethylimidazolium chloride and triethylamine.

Examples of a solvent to be used in a reaction with a thiol compound include, but not limited to, dichloromethane, acetonitrile, and toluene. These solvents can be used singly or in combination.

A production method of the present invention may optionally comprise a step of protecting and deprotecting a hydroxy group, an amino group, etc. in a side chain in a "saccharide having a non-protected sulfate group and/or a non-protected phosphate group" or a "compound comprising a saccharide having a sulfate group and/or a phosphate group".

Those skilled in the art can appropriately select a suitable protecting group from the protecting groups known in the art according to a selected reaction route.

Examples of a protecting group for a hydroxy group in the production method of the present invention may include a methyl group, a benzyl group, a benzoyl group, an acetyl (Ac) group, a trimethylsilyl (TMS) group, a triethylsilyl (TES) group, and a tert-butyldimethylsilyl (TBS or TBDMS) group. Examples of a protecting group for an amino group may include liposoluble protecting groups of a carbonate type or an amide type, such as a 9-fluorenylmethoxycarbonyl (Fmoc) group, a t-butyloxycarbonyl (Boc) group, a benzyl group, an allyloxycarbonyl (Alloc) group, a 2,2,2-trichloroethoxycarbonyl (troc) group, an allyloxycarbonyl group, and an acetyl group.

According to the production method of the present invention, unlike the conventional synthesis method, it is not necessary to protect/deprotect a sulfate group or a phosphate group, so that a sulfated saccharide, a phosphorylated saccharide, and a sulfated/phosphorylated saccharide, which have a controlled structure, can be produced more easily. Further, since it is not necessary to protect/deprotect a sulfate group or a phosphate group, a reaction route can be designed without considering protection of a sulfate group or a phosphate group. This leads to a dramatic increase in a protecting group usable in a reaction route and a reaction route, so that a sulfated saccharide, a phosphorylated saccharide, and a sulfated/phosphorylated saccharide or a compound containing the same can be produced more easily and efficiently than before, and that a type of a sulfated saccharide, a phosphorylated saccharide, and a sulfated/phosphorylated saccharide, or a compound containing the same, which have heretofore been difficult to synthesize, can now be synthesized. Further, the production method of the present invention is quite useful for synthesizing a sulfated saccharide, a phosphorylated saccharide, and a sulfated/phosphorylated saccharide having a long-chain uniform structure, or a compound containing the same.

It should be noted that the terms used herein are used for illustrating a specific embodiment, and are not intended to limit the invention.

In addition, the term "contain" used herein intends that there exists the described item (member, step, element, figure, etc.), and does not exclude the presence of not described items (members, steps, elements, figure, etc.), unless the context clearly requires a different understanding.

Unless otherwise defined, all terms (including technical terms and scientific terms) used herein have the same meaning as broadly understood by those skilled in the art to which the present invention belongs. The terms used herein should be interpreted as having meaning consistent with the meaning in this description and in the related technical field unless specifically defined otherwise, and should not be interpreted in an idealized or excessively formal sense.

It is understood that although the terms first, second, etc. may be used to express various elements, these elements should not be limited by these terms. These terms are only used to distinguish one element from another element, and, for example, it is possible without departing from the scope of the present invention that the first element is termed a second element, and likewise the second element is termed a first element.

The present invention will be described below more particularly by way of Examples, provided that the present invention can be embodied by various modes, and should not be interpreted as limited to Examples described here.

EXAMPLES

Example 1 (Production of Sulfated Saccharide by Condensation of Sulfated Monosaccharides)

As shown in the following reaction equation, a monosaccharide having a non-protected sulfate group at the position of the 5-position carbon atom and having a leaving group at the position of the 1-position carbon atom was prepared. The compound number shown after the name of a compound in a preparation example indicates the compound number shown in the following reaction equation.

Synthesis route of sulfated monosaccharide monomer

[Formula 12]

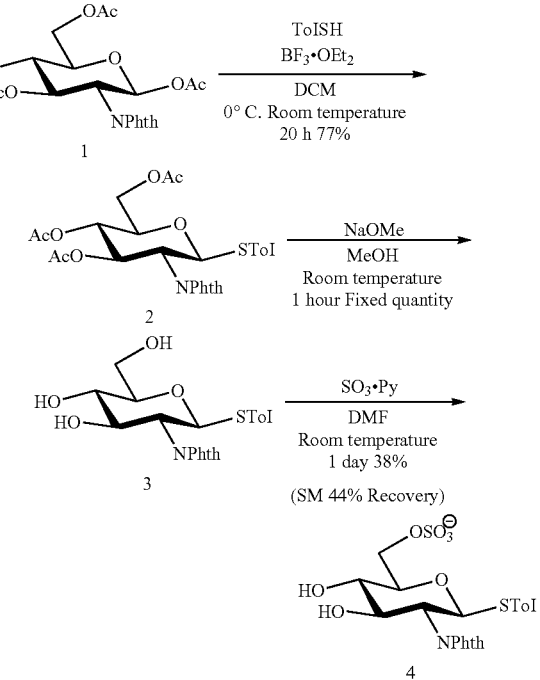

Thioglycoside 2

Under an argon atmosphere, the raw material 1 (4.0 g, 8.4 mmol) was dissolved in dry DCM. Then, the solution was cooled on ice. BF$_3$—OEt$_2$ (3.5 mL, 28 mmol) and p-toluenethiol (1.4 g, 11 mmol) were added, the mixture was returned to room temperature, and the reaction was carried out for 20 hours. Et$_3$N (3.5 mL, 25 mmol) was added to quench the reaction, and the reaction solution was diluted with DCM and washed with a saturated aqueous solution of NaHCO$_3$ and a saturated aqueous solution of NaCl. The organic layer was dried over sodium sulfate, then filtered, and concentrated. The reagent was removed using a silica gel column (from AcOEt/Hex=1/2 to AcOEt/Hex=2/1), and recrystallization from hot ethanol was performed to obtain Thioglycoside 2 as a white solid. $^1$H NMR (400 MHz CDCl$_3$) 7.87 (m, 2H), 7.76 (m, 2H), 7.30 (d, 2H, J=7.8 Hz), 7.08 (d, 2H, J=7.8 Hz), 5.78 (t, 1H, J=9.7 Hz), 5.65 (d, 1H, J=10.7 Hz), 5.12 (5, 1H, 9.7 Hz), 4.36-4.25 (m, 2H), 4.20 (dd, 1H, J=1.3 Hz, J=12.2 Hz), 3.88 (m, 1H), 2.33 (s, 3H), 2.11 (s, 3H), 2.02 (s, 3H), 1.83 (s, 3H), ESI-MS[M+Na]$^+$ calcd for C$_{27}$H$_{27}$NO$_9$SNa: 564.1 found 564.1.

1-STol-2-NPhth-Glucose 3

Under an argon atmosphere, Thioglycoside 2 (462 mg, 0.85 mmol) was dissolved in methanol. Sodium methoxide (10.3 mg, 0.19 mmol) was added thereto, and the mixture was stirred for 60 min. DOWEX 50Wx8 was added to quench the reaction, and the DOWEX 50Wx8 was removed by filtration. The filtrate was concentrated to obtain the target substance 3 as a white solid. The same was used for the next reaction without performing further purification. $^1$H NMR (400 MHz MeOD) 7.94-7.82 (m, 4H), 7.28 (d, 2H, J=8.2 Hz), 7.05 (d, 2H, J=8.2 Hz), 5.52 (d, 1H, J=10.4 Hz), 4.24 (dd, 1H, J=8.1 Hz, J=10.2 Hz), 4.08 (t, 1H, J=10.2 Hz), 3.94 (dd, 1H, J=1.8 Hz, J=12.0 Hz), 3.75 (dd, 1H, J=5.3 Hz, J=12.0 Hz), 3.48-3.39 (m, 2H), 2.28 (s, 3H), ESI-MS[M+Na]$^+$ calcd for C$_{21}$H$_{21}$NO$_6$SNa: 438.1 found 438.1.

1-STol-2-NPhth-6-OSO$_3$Na-Glucose 4

Under an argon atmosphere, 1-STol-2-NPhth-Glucose 3 (186 mg, 0.45 mmol) and SO$_3$—Py (76.6 mg, 0.48 mmol) were dissolved in DMF (9.6 mL), and the solution was stirred for 3.5 hours. An excess amount of a saturated aqueous solution of NaHCO$_3$ was added, the mixture was vigorously stirred for 1 hour, and then the reaction solution was concentrated. Silica gel column purification (AcOEt/MeOH/H$_2$O=6/2/1) was performed to obtain the raw material 3 (82.5 mg, 44%) and the target substance 4 (88.9 mg, 38%). $^1$H NMR (400 MHz D$_2$O) 7.95-7.75 (m, 4H), 7.25 (d, 2H, J=8.1 Hz), 7.08 (d, 2H, J=8.1 Hz), 5.64 (d, 1H, J=10.2 Hz), 4.42 (dd, 1H, J=1.8 Hz, J=11.4 Hz), 4.33-4.36 (m, 2H), 4.13 (t, 1H, 10.28 Hz), 3.93 (m, 1H), 3.62 (t, 1H, J=9.55 Hz), 2.23 (s, 3H), ESI-MS[M−Na]$^−$ calcd for C$_{21}$H$_{20}$NO$_9$S$_2$: 494.1 found 493.7.

The sulfated disaccharide 5 was prepared from the sulfated saccharide 4 as shown in the following reaction equation.

Polymerization

Under an argon atmosphere, the sulfated saccharide 4 (117 mg, 0.23 mmol) was dissolved in acetonitrile, molecular sieve 3A was added, and the mixture was cooled on ice. TfOH (1.9 μL) and N-iodosuccinimide (51.2 mg) were dissolved in acetonitrile (1 mL), the solution was dropped into the previous saccharide solution, and the mixture was stirred for 30 min. After returning to normal temperature and stirring overnight, the reaction solution was applied as it was to a silica gel column (AcOEt/MeOH=3/1) to remove the raw material and the reagent. Thereafter, the sulfated disaccharide 5 was isolated by HPLC. $^1$H NMR (400 MHz D$_2$O) 7.97-7.60 (m, 8H), 5.34 (d, 1H, J=8.42 Hz), 5.27 (d, 1H, J=8.60 Hz), 4.59 (dd, 1H, J=8.4 Hz, J=10.9 Hz), 4.46-4.21 (m, 4H), 4.10 (dd, 1H, J=8.7 Hz, J=10.6 Hz), 4.05-3.93 (m, 2H), 3.86 (m, 2H), 3.70 (t, 1H, J=9.0 Hz), 3.58 (t, 1H, J=9.3 Hz), ESI-MS[M−2Na+H]$^−$ calcd for C$_{28}$H$_{27}$N$_2$O$_{19}$S$_2^−$: 759.1 found: 758.7.

Example 2 (Production of Sulfated Saccharide by Condensation of Sulfated Disaccharides)

As shown in the following reaction equation, a disaccharide having a non-protected sulfate group at the position of the 6-position carbon atom of the reducing terminal and having a leaving group at the position of the 1-position carbon atom was prepared. The compound number shown after the name of a compound in a preparation example indicates the compound number shown in the following reaction equation.

Synthesis of disaccharide having sulfate group

[Formula 14]

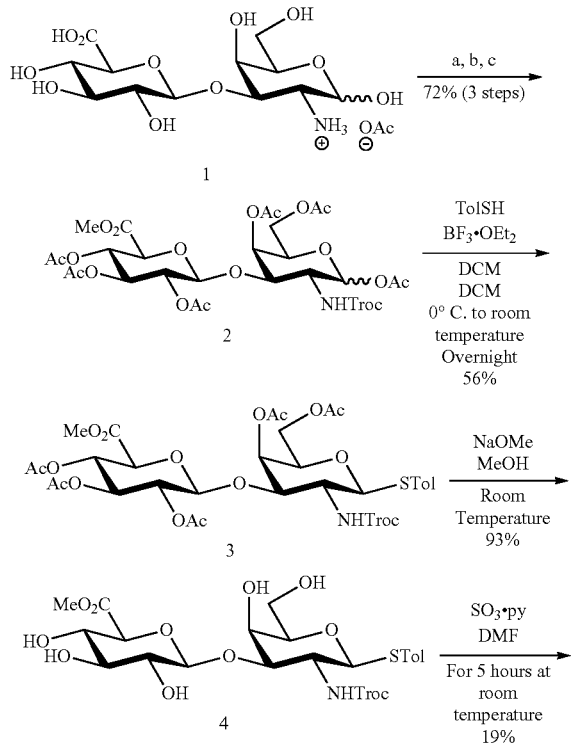

Polymerization of sulfated saccharide 4

[Formula 13]

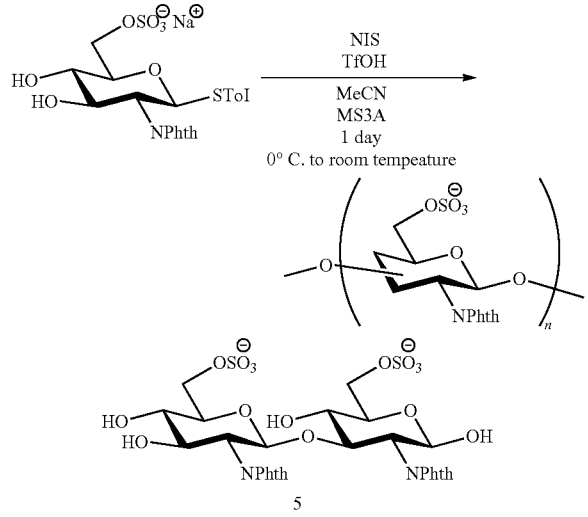

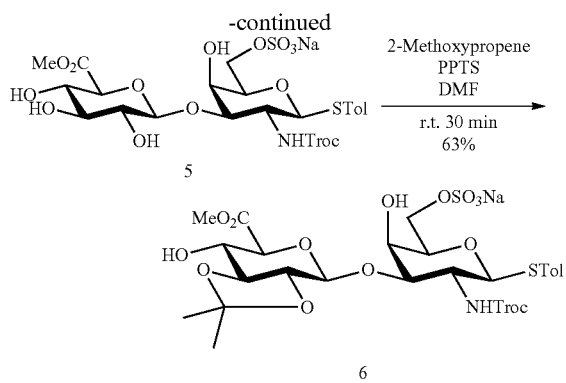

a: AcCl, MeOH 0° C. to room temperature 20 h
b: TrocCl, NaHCO₃, H₂O, r.t, 2 h
c: Ac₂O, Pyridine, DMAP, r.t, 3 h Chondrosamine Acetate 1

Chondrosamine 1 was prepared in accordance with the previous report (Jean-Claude Jacquinet, et al., Angew. Chem. Int. Ed 2006, 45, 2574-2578).

2-NHTroc Chondrosamine Methyl Ester Peracetate 2

Under an argon atmosphere, acetyl chloride (120 µL, 1.6 mmol) was added to methanol (13 mL), and the mixture was stirred in an ice bath for 30 min. Chondrosamine acetate 1 (340 mg, 0.82 mmol) was added, and the mixture was stirred for 20 hours. The reaction solution was concentrated, methanol was added, and the concentration was repeated multiple times. The concentrated residue and NaHCO₃ (240 mg, 2.85 mmol) were dissolved in water (7.4 mL), the solution was vigorously stirred for 30 min. 2,2,2-Trichloroethyl chloroformate (260 µL, 1.9 mmol) was dropped slowly, and the mixture was stirred for 2 hours. Thereto, DOWEX 50Wx8 was added to quench the reaction, and the DOWEX 50Wx8 was removed by filtration. The DOWEX 50Wx8 was washed with methanol three times. The filtrate was concentrated and subjected to silica gel column purification (AcOEt/MeOH/H₂O=6/2/1) to obtain N-Troc chondrosamine methyl ester (353 mg, 79%). Under an argon atmosphere, N-Troc chondrosamine methyl ester (350 mg, 0.65 mmol) was dissolved in Ac₂O/pyridine (1/1, 7 mL). N,N-Dimethyl-4-aminopyridine (7.9 mg, 0.065 mmol) was added, and the mixture was stirred at room temperature for 3 hours. Thereafter, the reaction solution was cooled on ice, and excess methanol was slowly added to quench the reaction. The reaction solution was concentrated and subjected to silica gel purification (AcOEt/Hex=1/1) to obtain the target substance 2 (470 mg, 3 steps, 72%, α/β nearly 1:1). $^1$H NMR (400 Hz CDCl₃) 6.57 (d, J=6.8 Hz, β-anomer), 6.32 (d, J=3.04, α-anomer), 5.80 (t, J=8.6 Hz), 5.44-4.96 (m), 4.89-4.54 (m), 4.34 (dt, J=3.5 Hz, J=10.5 Hz), 4.30-3.95 (m), ESI-MS[M+Na]⁺ calcd for $C_{28}H_{36}{}^{35}Cl_3NO_{19}Na$: 818.1 found 818.1.

1-STol-2-NHTroc Chondrosamine Methyl Ester Peracetate 3

Under an argon atmosphere, N-Troc chondrosamine methyl ester peracetate 2 (717 mg, 0.90 mmol) and p-toluenethiol (111 mg, 0.89 mmol) were dissolved in DCM, and the solution was cooled on ice. BF₃—OEt₂ (338 µL, 2.7 mmol) was dropped, and the mixture was stirred for 30 min. Thereafter, the mixture was stirred overnight at room temperature. Et₃N (375 µL, 2.7 mmol) was added to quench the reaction. The reaction solution was diluted by adding DCM and washed with a saturated aqueous solution of NaHCO₃ and a saturated aqueous solution of NaCl. The organic layer was dried over sodium sulfate, then filtered, and concentrated. The residue was subjected to silica gel column purification (from AcOEt/Hex=1/2 to AcOEt/Hex=1/1) to obtain the target compound 3 as a white solid (436 mg, 56%). 1H NMR (400 MHz CDCl3) 7.41 (d, 2H, J=8.0 Hz), 7.11 (d, 2H, J=8.0 Hz), 5.41 (d, 1H, J=7.9 Hz), 5.38 (d, 1H, J=2.7 Hz), 5.22-5.13 (m, 2H), 4.99-4.93 (m, 2H), 4.86 (d, 1H, J=12.1 Hz), 4.73 (d, 1H, J=7.9 Hz), 4.64 (d, 1H, J=12.1 Hz), 4.31 (dd, 1H, J=3.1 Hz, J=10.5 Hz), 4.19-3.95 (m, 3H), 3.86 (t, 1H, J=6.42 Hz), 3.75 (s, 3H), 3.65 (m, 1H), 2.34 (s, 3H), 2.08 (s, 3H), 2.05 (s, 3H), 2.04 (s, 3H), 2.01 (s, 3H), 1.99 (s, 3H) ESI-MS[M+Na]⁺ calcd for C33H4035Cl3NO17SNa. 882.1 found 882.1.

1-STol-2NHTroc Chondrosamine Methyl Ester 4

Under an argon atmosphere, 1-STol-2-NHTroc chondrosamine methyl ester peracetate 3 (510 mg, 0.59 mmol) was dissolved in dry methanol. Sodium methoxide was added, and the mixture was stirred at room temperature for 1.5 hours. DOWEX 50Wx8 was added to quench the reaction, and the mixture was filtered and concentrated. The residue was subjected to silica gel column purification (AcOEt/MeOH=50/3) to obtain the target compound 4 as a white solid. 1H NMR (400 MHz D2O) 7.36 (d, 2H, J=8.1 Hz), 7.16 (d, 2H, J=8.1 Hz), 4.89 (d, 1H, J=12.4 Hz), 4.74 (d, 1H), 4.59 (d, 1H, J=12.4 Hz), 4.54 (d, 1H, J=8.15 Hz), 4.07 (d, 1H, J=2.56 Hz), 3.96 (d, 1H, J=9.7 Hz), 3.73 (s, 3H), 3.71-3.57 (m, 3H), 3.48 (t, 1H, J=9.2 Hz), 3.41 (t, 1H, J=9.1 Hz), 3.28 (dd, 1H, J=7.92 Hz, J=8.79 Hz), 2.24 (s, 3H), ESI-MS[M+Na]⁺ calcd for C23H3035Cl3NO12SNa: 672.0 found 672.0.

1-STol-2NHTroc-6-OSO₃Na Chondrosamine Methyl Ester 5

Under an argon atmosphere, 1-STol-2NHTroc chondrosamine methyl ester 4 and SO₃—Py were dissolved in DMF, and the solution was stirred at room temperature overnight. Thereafter, an excess amount of saturated NaHCO₃ was added, and the mixture was vigorously stirred for 30 min. The reaction solution was concentrated and subjected to silica gel column purification (AcOEt/MeOH/H₂O=6/1/1) to obtain the target substance 5. 1H NMR (400 MHz MeOD) 7.42 (d, 2H, J=8.1 Hz), 7.13 (d, 2H, J=8.1 Hz), 4.90 (d, 1H, J=12.1 Hz), 4.73 (d, 1H, J=10.3 Hz), 4.67 (d, 1H, J=12.1 Hz), 4.52 (d, 1H, J=7.5 Hz), 4.20 (dd, 1H, J=5.9 Hz, J=10.7 Hz), 4.16 (dd, 1H, J=6.4 Hz, J=10.6 Hz), 4.09 (d, 1H, 2.7 Hz), 3.91 (t, 1H, J=10.3 Hz), 3.86-3.74 (m, 6H), 3.55 (5, 1H, J=9.1 Hz), 3.40-3.26 (m, 2H), 2.31 (s, 3H), ESI-MS[M−H]⁻ calcd for C23H2935Cl3NO15S2: 728.0 found 727.8.

1-STol-2-NHTroc-6-OSO₃Na-2',3'-O-Isop Chondrosamine Methyl Ester 6

Under an argon atmosphere, 1-STol-2NHTroc-6-OSO₃Na chondrosamine methyl ester 5 was dissolved in DMF. 2-Methoxypropene and pyridinium p-toluenesulfonate were added, and the mixture was stirred at room temperature for 30 min. Saturated NaHCO₃ was added to quench the reaction, and then the solution was concentrated. The residue was subjected to silica gel column purification (AcOEt/MeOH/H₂O=6/1/1) to obtain the target substance 6. 1H NMR (400 MHz DMSO) 7.32 (d, 2H, J=8.2 Hz), 7.11 (d, 2H, J=8.2 Hz), 5.77 (d, 1H, J=5.6 Hz), 4.93 (d, 1H, J=7.9 Hz), 4.86 (d, 1H, J=12.1 Hz), 4.77 (d, 1H, J=4.8 Hz), 4.68-4.60 (m, 2H), 3.88-3.58 (m, 11H), 3.43 (t, 1H, J=9.1 Hz), 3.26 (t, 1H, J=8.3 Hz), 2.27 (s, 3H), ESI-MS[M+Na] calcd for C26H33Cl3NO15S2:768.0 found 767.8.

Next, the sulfated disaccharide 6 was polymerized as shown in the following reaction equation.

[Formula 15]

Polymerization reaction of disaccharide having sulfate group

[Formula 15]

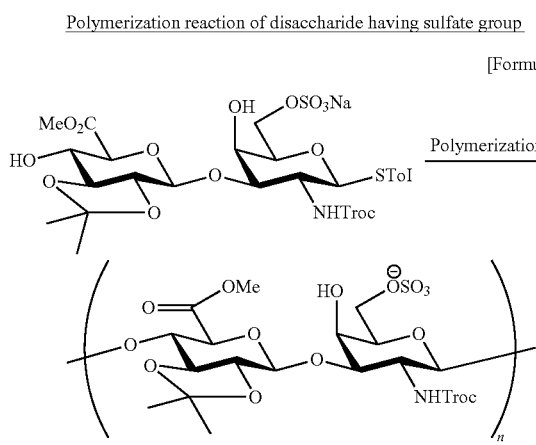

Under an argon atmosphere, 1-STol-2-NHTroc-6-OSO$_3$Na-2',3'-O-isop chondrosamine methyl ester 6 was dissolved in acetonitrile. Activated molecular sieve 3A was added thereto. DMTST was added to start the reaction. After 10 min, part of the solution was taken out, quenched with Et$_3$N, and then measured by ESI-MS. ESI-MS [M−2Na+H] calcd for $C_{38}H_{51}Cl_6N_2O_{30}S_2^-$: 1289.0 found: 1288.6.

Based on the results of ESI-MS, it was inferred that the product synthesized by the polymerization reaction had the following structure.

[Formula 16]

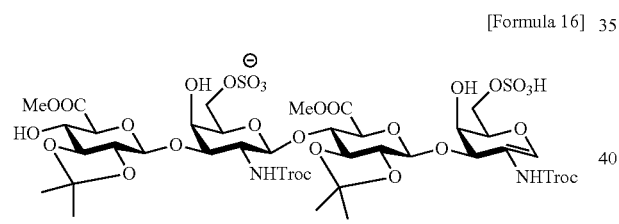

(Example 3) Synthesis of Sulfated Disaccharide (Glycosyl o-Hexynylbenzoate) Donor The sulfated disaccharide donor 6 having a non-protected sulfate group at the position of the 6-position carbon atom of the reducing terminal and having a leaving group at the position of the 1-position carbon atom was prepared as shown in the following reaction equation. The compound number shown after the name of a compound in a preparation example indicates the compound number shown in the following reaction equation.

[Formula 17]

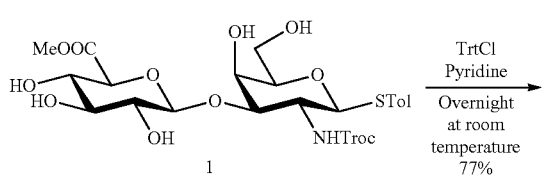

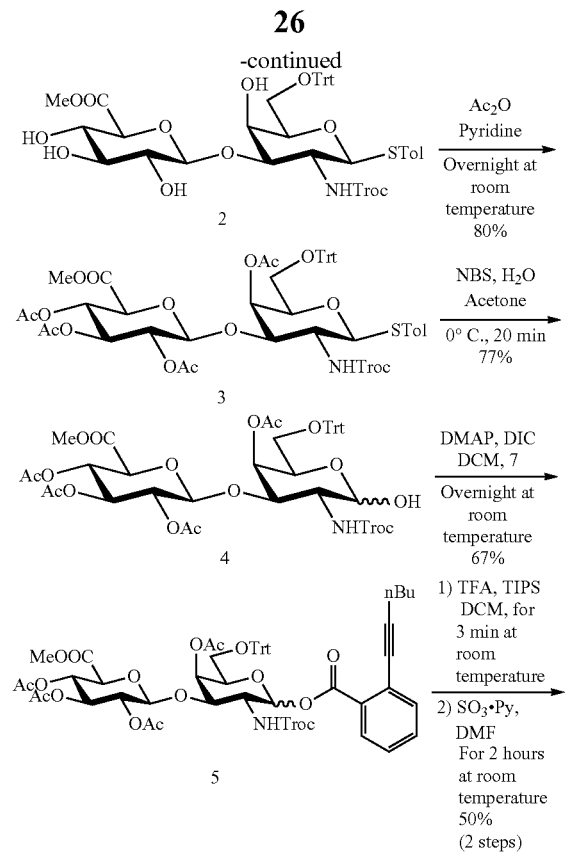

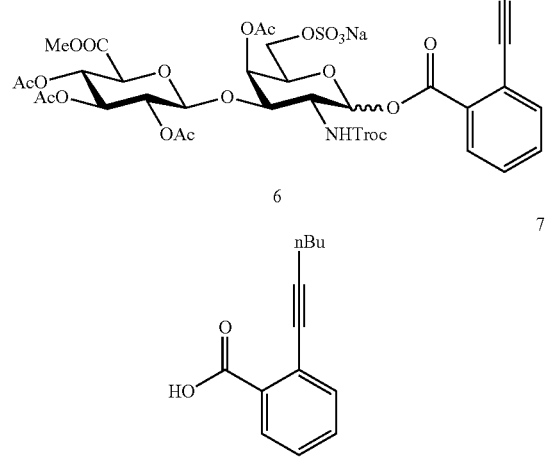

p-Tolyl(methyl-β-D-glucopyranosyluronate)-(1→3)-2-deoxy-1-thio-2-(2,2,2-trichloroethoxycarbonylamino)-6-O-triphenylmethyl-β-D-galactopyranoside 2 p-Tolyl(methyl-β-D-glucopyranosyluronate)-(1→3)-2-deoxy-1-thio-2-(2,2,2-trichloroethoxycarbonylamino)-β-D-galactopyranoside 1 (72 mg, 0.11 mmol) and triphenylmethyl chloride (34 mg, 0.12 mmol) were dissolved in pyridine (1.16 mL) under an argon atmosphere. After stirring overnight at 50° C., the reaction solution was concentrated. The concentrated residue was purified with a silica gel column (AcOEt:MeOH=50:3) to obtain the target substance 2 (90 mg, 0.09 mmol, 77%).

¹H NMR (400 Hz CDCl₃) 7.45-7.37 (m, 7H), 7.31-7.19 (m, 10H), 7.04 (d, J=8.0 Hz, 2H), 5.51 (d, J=8.1 Hz, 2H), 5.40 (d, J=2.85 Hz, 2H), 5.22-5.12 (m, 2H), 4.99-4.91 (m, 2H), 4.85 (d, J=12.2 Hz, 1H), 4.73 (d, J=7.9 Hz, 1H), 4.64 (d, J=12.2 Hz, 1H), 4.24 (dd, J=2.8 Hz, J=10.8 Hz, 1H), 3.99 (d, J=9.3 Hz, 1H), 3.76-3.61 (m, 5H), 3.31 (dd, J=6.9 Hz, J=9.9 Hz, 1H), 3.04 (dd, J=5.7 Hz, J=9.9 Hz, 3H), 2.30 (s, 3H) ESI-MS[M+Na]⁺ calcd for $C_{42}H_{44}{}^{35}Cl_3NNaO_{12}S$: 914.2 found 914.5 p-Tolyl(methyl-2,3,4-tri-O-acetyl-β-D-glucopyranosyluronate)-(1→3)-4-O-acetyl-2-deoxy-1-thio-2-(2,2,2-trichloroethoxycarbonylamino)-6-O-triphenylmethyl-β-D-galactopyranoside 3 p-Tolyl(methyl-β-D-glucopyranosyluronate)-(1→3)-2-deoxy-1-thio-2-(2,2,2-trichloroethoxycarbonylamino)-6-O-triphenylmethyl-β-D-galactopyranoside 2 (150 mg, 0.168 mmol) was dissolved in pyridine/acetic anhydride 1:1 (3.3 mL) under an argon atmosphere. After stirring overnight at room temperature, the reaction solution was cooled on ice, and excess methanol was slowly added to quench the reaction. The reaction solution was concentrated and purified with a silica gel column (AcOEt:Hex=2:3) to obtain the target substance 3 (177 mg, 0.167 mmol, 99%).

¹H NMR (400 Hz CDCl₃) 7.41 (d, J=7.8 Hz, 8H), 7.31-7.20 (m, 9H), 7.04 (d, J=7.7 Hz, 2H), 5.43-5.38 (m, 2H), 5.22-5.12 (m, 2H), 4.99-4.91 (m, 2H), 4.85 (d, J=12.1 Hz, 1H), 4.73 (d, J=7.8 Hz, 1H), 4.63 (d, J=12.1 Hz, 1H), 4.24 (dd, J=3.0 Hz, J=10.5 Hz, 1H), 3.99 (d, J=9.4 Hz, 1H), 3.70-3.61 (m, 4H), 3.31 (dd, J=7.0 Hz, J=9.8 Hz, 1H), 3.04 (dd, J=5.4 Hz, J=9.5 Hz, 1H), 2.31 (s, 3H), 2.04 (s, 3H), 2.01 (s, 3H), 2.00 (s, 3H), 1.88 (s, 3H) ESI-MS[M+Na]⁺ calcd for $C_{50}H_{52}{}^{35}Cl_3NNaO_{16}S$: 1082.2 found 1082.2

(Methyl-2,3,4-tri-O-acetyl-β-D-glucopyranosyluronate)-(1→3)-4-O-acetyl-2-deoxy-1-thio-2-(2,2,2-trichloroethoxycarbonylamino)-6-O-triphenylmethyl-β-D-galactopyranose 4 p-Tolyl(methyl-2,3,4-tri-O-acetyl-β-D-glucopyranosyluronate)-(1→3)-4-O-acetyl-2-deoxy-1-thio-2-(2,2,2-trichloroethoxycarbonylamino)-6-O-triphenylmethyl-β-D-galactopyranoside 3 (230 mg, 217 mmol) was dissolved in H₂O/acetone 1:10 (2.3 mL). The solution was cooled on ice, N-bromosuccinimide (116 mg, 0.65 mmol) was added, and the mixture was stirred for 20 min. The reaction solution was diluted with AcOEt, and the organic phase was washed with a saturated sodium bicarbonate solution and a saturated saline solution, and then dried over sodium sulfate. Sodium sulfate was removed by filtration, followed by concentration under reduced pressure. The residue was purified with a silica gel column (AcOEt:Hex=1:1) to obtain the target substance 4 (159 mg, 0.166 mmol, 77%).

¹H NMR α-anomer (400 Hz CDCl₃) 7.44-7.35 (m, 6H), 7.31-7.19 (m, 9H), 5.71 (d, J=9.0 Hz, 1H), 5.49 (d, J=2.2 Hz, 1H) 5.27-5.14 (m, 3H), 4.88-4.70 (m, 2H), 4.70-4.60 (m, 1H), 4.33 (t, J=6.6 Hz, 1H), 4.21 (dd, J=3.1 Hz, J=10.5 Hz, 1H), 4.15-3.97 (m, 2H), 3.74-3.65 (m, 4H), 3.17 (dd, J=6.6 Hz, J=9.2 Hz, 1H), 3.08-2.99 (m, 1H), 2.10-2.00 (m, 12H) ESI-MS[M+Na]⁺ calcd for $C_{43}H_{46}{}^{35}Cl_3NNaO_{17}$: 976.2 found 976.7

(Methyl-2,3,4-tri-O-acetyl-β-D-glucopyranosyluronate)-(1→3)-4-O-acetyl-2-deoxy-1-thio-2-(2,2,2-trichloroethoxycarbonylamino)-6-O-triphenylmethyl-β-D-galactopyranosyl o-hexynylbenzoate 5

Methyl-2,3,4-tri-1-acetyl-β-D-glucopyranosyluronate)-(1→3)-4-O-acetyl-2-deoxy-1-thio-2-(2,2,2-trichloroethoxycarbonylamino)-6-O-triphenylmethyl-β-D-galactopyranose 4 (159 mg, 0.166 mmol) and o-hexynylbenzoic acid 7 (101 mg, 0.499 mmol) were dissolved in DCM (1.7 mL) under an argon atmosphere. N,N-dimethylaminopyridine (2 mg, 0.02 mmol) and N,N'-diisopropylcarbodiimide (78 µL, 0.499 mmol) were added, and the mixture was stirred at room temperature overnight. The reaction solution was diluted with DCM, washed with a saturated sodium bicarbonate solution and a saturated saline solution, and then dried over sodium sulfate. The sodium sulfate was removed by filtration, followed by concentration under reduced pressure. The residue was purified with a silica gel column (AcOEt:Hex=2:3) to obtain the target substance 5 (126 mg, 0.11 mmol, 67%). ¹H NMR α-anomer (400 Hz CDCl₃) 8.02 (d, J=8, 2 Hz, 1H), 7.63 (d, J=7.9 Hz, 1H), 7.53 (dt, J=1.3 Hz, J=7.5 Hz 1H), 7.47-7.41 (m, 1H) 7.40-7.35 (m, 7H), 7.29-7.26 (m, 4H), 7.21-7.15 (m, 4H), 6.45 (d, J=3.3 Hz, 1H), 6.02 (d, J=8.7 Hz, 1H), 5.63 (b, 1H), 5.26-5.19 (m, 2H), 4.87 (d, J=7.6 Hz, 1H), 4.81 (d, J=12.0 Hz, H), 4.54-4.49 (m, 2H), 4.38-4.32 (m, 1H), 4.29-4.24 (m, 1H), 4.09 (d, J=9.3 Hz, 1H), 3.43 (s, 3H), 3.31 (dd, J=5.5 Hz, J=9.1 Hz, 1H), 2.97 (t, J=9.1 Hz, 1H), 2.67-2.49 (m, 2H), 2.16 (s, 3H), 2.06 (s, 6H), 1.85 (s, 3H), 1.66-1.57 (m, 2H), 1.51-1.47 (m, 2H), 0.89 (t, J=7.3 Hz, 3H) ESI-MS[M+Na]⁺ calcd for $C_{56}H_{58}{}^{35}Cl_3NNaO_{18}$: 1160.3 found 1160.9

(Methyl-2,3,4-tri-O-acetyl-β-D-glucopyranosyluronate)-(1→3)-4-O-acetyl-2-deoxy-6-O-sulfo-1-thio-2-(2,2,2-trichloroethoxycarbonylamino)-β-D-galactopyranosyl o-hexynylbenzoate, monosodium salt 6

(Methyl-2,3,4-tri-O-acetyl-β-D-glucopyranosyluronate)-(1→3)-4-O-acetyl-2-deoxy-1-thio-2-(2,2,2-trichloroethoxycarbonylamino)-6-O-triphenylmethyl-β-D-galactopyranosyl o-hexynylbenzoate 5 (50.0 mg, 0.044 mmol) was dissolved in DCM (440 µL). Trifluoroacetic acid (44 µL) and triisopropylsilane (45 µL) were added, and the mixture was stirred at room temperature for 3 min. An excess saturated sodium bicarbonate solution was added to quench the reaction, followed by extraction with AcOEt. The organic phase was washed with a saturated saline solution and then dried over sodium sulfate. The sodium sulfate was removed by filtration, followed by concentration under reduced pressure. The residue was dissolved in DMF (440 µL) under an argon atmosphere, SO3-Py (14 mg, 0.088 mmol) was added, and the solution was stirred. After 2 hours, a saturated sodium bicarbonate solution (1.0 mL) was added to the reaction solution, and the mixture was stirred for another 30 min. The reaction solution was concentrated under reduced pressure and then purified with a silica gel column (AcOEt:MeOH=10:1) to obtain the target substance 6 (29.8 mg, 0.030 mmol, 68%).

¹H NMR (a anomer)(400 Hz MeOD) 8.06-8.00 (m, 1H), 7.55-7.49 (m, 2H), 7.45-7.40 (m, 1H), 6.50 (d, J=2.47 Hz, 1H), 5.60 (b, 1H), 5.26 (t, J=9.2 Hz 1H), 5.09 (t, J=9.8 Hz, 1H), 4.96-4.87 (m, 3H), 4.65-4.58 (m, 2H), 4.32-4.28 (m, 2H), 4.20 (d, J=9.8 Hz, 1H), 4.13-4.07 (m, 1H), 3.99-3.93 (m, 1H), 3.73 (s, 3H), 2.48 (t, J=6.8, 2H), 2.15 (s, 3H), 2.02 (s, 3H), 1.99 (s, 3H), 1.97 (s, 3H), 1.67-1.50 (m, 4H), 0.99 (t, J=7.2 Hz, 3H) ESI-MS[M-H]⁻ calcd for $C_{37}H_{43}{}^{35}Cl_3NO_{21}S$: 974.1 found 973.9

Synthesis of Disaccharide Acceptor

The disaccharide acceptor 11 was prepared according to the following reaction equations. The compound number shown after the name of a compound in a preparation example indicates the compound number shown in the following reaction equation.

Synthesis of acceptor

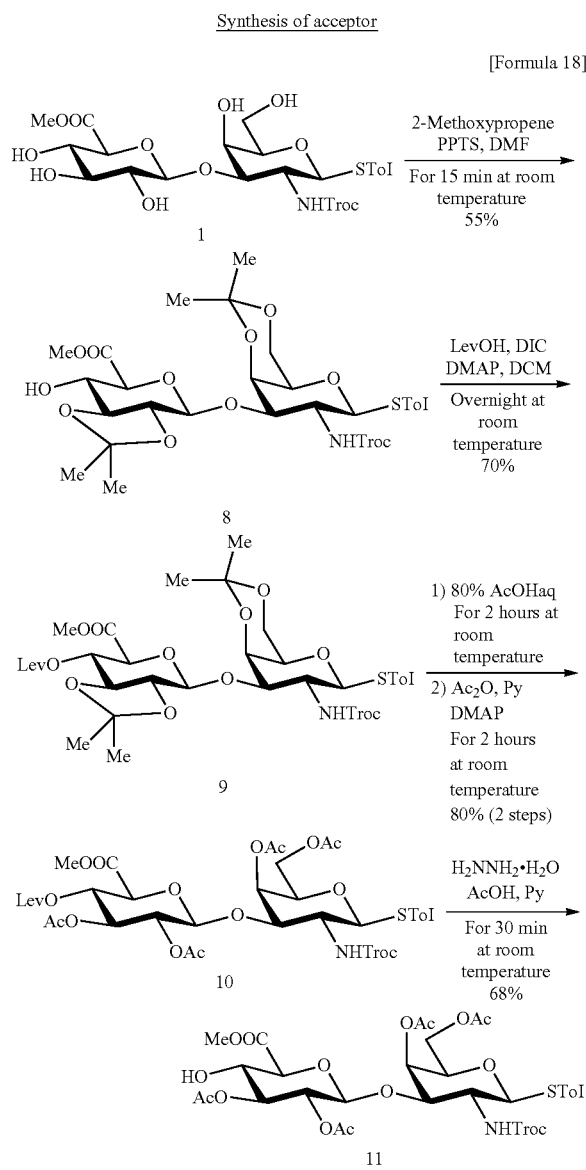

[Formula 18]

p-Tolyl(methyl 2,3-O-isopropylidene-β-D-glucopyranosyluronate)-(1→3)-2-deoxy-4,6-O-isopropylidene-1-thio-2-(2,2,2-trichloroethoxycarbonylamino)-β-D-galactopyranoside 8 p-Tolyl(methyl-β-D-glucopyranosyluronate)-(1→3)-2-deoxy-1-thio-2-(2,2,2-trichloroethoxycarbonylamino)-β-D-galactopyranoside 1 (332 mg, 0.51 mmol) was dissolved in DMF (5.1 mL) under an argon atmosphere. PPTS (64 mg, 0.25 mmol) and 2-methoxypropene (490 μL, 5. mmol) were added, and the mixture was stirred at room temperature for 15 min. The reaction system was diluted with ethyl acetate, washed with a saturated sodium bicarbonate solution and a saturated saline solution, and then dried over sodium sulfate. The sodium sulfate was removed by filtration, followed by concentration under reduced pressure. The residue was purified with a silica gel column (AcOEt:Hex=2:3) to obtain the target substance 8 (204 mg, 0.279 mmol, 55%).

$^1$H NMR (400 Hz CDCl$_3$) 7.56 (d, J=8.0 Hz, 2H), 7.10 (d, J=8.0 Hz, 2H), 5.58 (d, J=6.5 Hz, 1H), 5.28 (d, J=10.0 Hz, 1H), 4.88 (d, J=7.66 Hz 1H), 4.74 (d, J=12.0 Hz, 1H), 4.69 (d, J=12.0 Hz, 1H), 4.08-4.00 (m, 3H), 3.84 (s, 3H), 3.68 (d, J=8.8 Hz, 1H), 3.49-3.42 (m, 3H), 3.37 (dd, J=7.7 Hz, J=9.1 Hz 1H), 2.33 (s, 3H), 1.44-1.39 (m, 12H) ESI-MS[M+Na]$^+$ calcd for C$_{29}$H$_{38}$$^{35}$Cl$_3$NNaO$_{12}$S: 752.1 found 752.1 p-Tolyl(methyl 2,3-O-isopropylidene-4-O-levulinoyl-β-D-glucopyranosyluronate)-(1→3)-2-deoxy-4,6-O-isopropylidene-1-thio-2-(2,2,2-trichloroethoxycarbonylamino)-β-D-galactopyranoside 9 p-Tolyl(methyl 2,3-O-isopropylidene-β-D-glucopyranosyluronate)-(1→3)-2-deoxy-4,6-O-isopropylidene-1-thio-2-(2,2,2-trichloroethoxycarbonylamino)-β-D-galactopyranoside 8 (63 mg, 0.086 mmol) was dissolved in DCM (862 μL) under an argon atmosphere. DMAP (2 mg, 0.02 mmol), LevOH (26 μL, 0.26 mmol), and DIC (40 μL, 0.26 mmol) were added, and the mixture was stirred at room temperature overnight. The reaction solution was diluted with ethyl acetate, washed with a saturated sodium bicarbonate solution and a saturated saline solution, and then dried over sodium sulfate. The sodium sulfate was removed by filtration, followed by concentration under reduced pressure. The residue was purified with a silica gel column (AcOE:Hex=3:2) to obtain the target substance 9 (50 mg, 0.060 mmol, 70%).

$^1$H NMR (400 Hz CDCl$_3$) 7.55 (d, J=8.0 Hz, 2H), 7.11 (d, J=8.0 Hz, 2H), 5.32-5.16 (m, 3H), 4.83-4.78 (m, 2H), 4.62 (d, J=12.1 Hz 1H), 4.46 (d, J=9.8 Hz, 1H), 4.37 (d, J=2.8 Hz, 1H), 4.05-3.95 (m, 2H), 3.88-3.78 (m, 2H), 3.72 (s, 3H), 3.58-3.47 (m, 2H), 3.42 (b, 1H), 2.79-2.59 (m, 4H), 2.33 (s, 3H), 2.20 (s, 3H), 1.15 (s, 6H), 1.13 (s, 6H) ESI-MS[M+K]$^+$ calcd for C$_{34}$H$_{44}$$^{35}$Cl$_3$KNO$_{14}$S: 866.1 found 866.0 p-Tolyl(methyl 2,3-di-O-acetyl-4-O-levulinoyl-β-D-glucopyranosyluronate)-(1→3)-4,6-di-O-acetyl-2-deoxy-1-thio-2-(2,2,2-trichloroethoxycarbonylamino)-β-D-galactopyranoside 10 p-Tolyl(methyl 2,3-O-isopropylidene-4-O-levulinoyl-R-D-glucopyranosyluronate)-(1→3)-2-deoxy-4,6-O-isopropylidene-1-thio-2-(2,2,2-trichloroethoxycarbonylamino)-β-D-galactopyranoside 9 (227 mg, 0.274 mmol) was dissolved in a 80% acetic acid aqueous solution (2.74 mL), and the solution was stirred at room temperature for 2 hours. After the reaction, the reaction solution was neutralized with a saturated sodium bicarbonate solution (approx. 3 mL) and extracted three times with ethyl acetate. The organic phase was washed with a saturated saline solution and dried over sodium sulfate. The sodium sulfate was removed by filtration, followed by concentration under reduced pressure. Under an argon atmosphere, the residue was dissolved in acetic anhydride (1.4 mL) and pyridine (1.4 mL), DMAP (3 mg, 0.03 mmol) was added, and the mixture was stirred at room temperature. The reaction solution was cooled on ice, and excess methanol was added to quench the reaction. After concentration under reduced pressure, purification was carried out with a silica gel column (AcOEt:Hex=1:1) to obtain the target substance 10 (201 mg, 0.219 mmol, 80%).

$^1$H NMR (400 Hz CDCl$_3$) 7.36 (d, J=8.0 Hz, 2H), 7.05 (d, J=8.0 Hz, 2H), 5.59 (d, J=8.3 Hz, 1H), 5.33 (d, J=3.0 Hz, 1H), 5.17-5.09 (m, 2H), 4.96-4.87 (m, 2H), 4.79 (d, J=12.1 Hz, 1H), 4.71 (d, J=7.8 Hz, 1H), 4.63 (d, J=7.8 Hz, 1H), 4.23 (dd, J=3.0 Hz, J=10.3 Hz, 1H), 4.09 (dd, J=5.3 Hz, J=11.8 Hz, 1H), 4.00-3.90 (m, 2H), 3.81 (dd, J=5.7 Hz, J=6.8 Hz, 1H), 3.72-3.61 (m, 4H), 2.70-2.62 (m, 2H), 2.47-2.40 (m, 2H), 2.29 (s, 3H), 2.10 (s, 3H), 2.03 (s, 3H), 2.01 (s, 3H), 2.00 (s, 3H), 1.99 (s, 3H) ESI-MS [M+Na]$^+$ calcd for C$_{36}$H$_{44}$$^{35}$Cl$_3$NNaO$_{18}$S: 938.1 found 938.1 p-Tolyl(methyl 2,3-di-O-acetyl-β-D-glucopyranosyluronate)-(1→3)-4,6-di-O-acetyl-2-deoxy-1-thio-2-(2,2,2-trichloroethoxycarbonylamino)-β-D-galactopyranoside 11 p-Tolyl(methyl 2,3-di-O-acetyl-4-O-levulinoyl-β-D-glucopyranosyluronate)-(1→3)-4,6-di-O-acetyl-2-deoxy-1-thio-2-(2,2,2-trichloroethoxycarbonylamino)-β-D-galactopyranoside 10 (201 mg, 0.219 mmol) was dissolved in pyridine (1.09 mL) and acetic acid (1.09 mL) under an argon atmosphere. Hydrazine monohydrate (13 μL, 0.263 mmol) was added, and the mixture was stirred at room temperature for 30 min. The reaction solution was diluted with ethyl acetate, washed with a saturated sodium bicarbonate solution and a saturated saline solution, and then dried over sodium sulfate. The sodium sulfate was removed by filtration, followed by concentration under reduced pressure. The residue was purified with a silica gel column (AcOEt: Hex=3:2) to obtain the target substance 11 (121 mg, 0.148 mmol, 68%). $^1$H NMR (400 Hz CDCl$_3$) 7.41 (d, J=8.0 Hz, 2H), 7.11 (d, J=8.0 Hz, 2H), 5.44 (d, J=2.8 Hz, 1H), 5.05-4.99 (m, 2H), 4.89-4.80 (m, 2H), 4.71-4.65 (m, 2H), 4.37-4.32 (m, 1H), 4.18-4.02 (m, 2H), 3.96-3.83 (m, 6H), 3.62-3.52 (m, 1H), 2.34 (s, 3H), 2.07 (s, 3H), 2.06 (s, 3H), 2.05 (s, 3H), 2.04 (s, 3H) ESI-MS[M+K]$^+$ calcd for C$_{31}$H$_{38}$$^{35}$Cl$_3$KNO$_{16}$S: 856.6 found 856.0

(Synthesis Example 1) (Synthesis of Sulfated Tetrasaccharide)

The sulfated disaccharide donor 6 and the disaccharide acceptor 11 prepared as above were condensed according to the following reaction equation to prepare the target sulfated tetrasaccharide 12. The compound number shown after the name of a compound in a preparation example indicates the compound number shown in the following reaction equation.

[Formula 19]

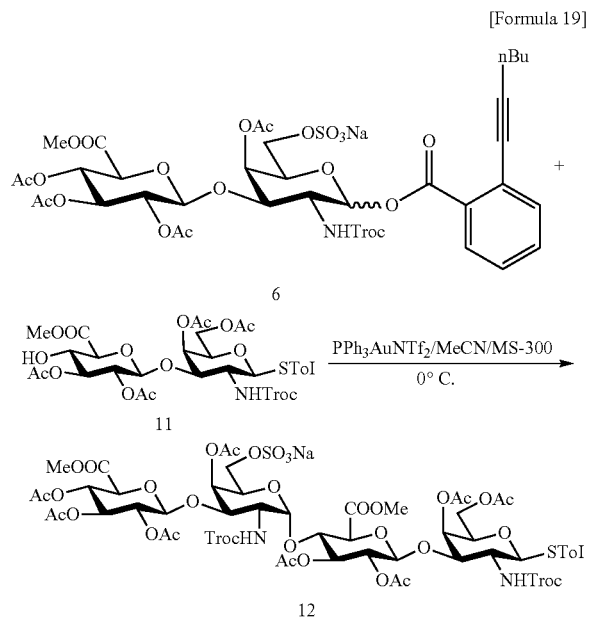

p-Tolyl(methyl 2,3-di-O-acetyl-β-D-glucopyranosyluronate)-(1→3)-4,6-di-O-acetyl-2-deoxy-1-thio-2-(2,2,2-trichloroethoxycarbonylamino)-3-D-galactopyranoside 11 (12.0 mg, 0.015 mmol) and (methyl-2,3,4-tri-O-acetyl-β-D-glucopyranosyluronate)-(1→3)-4-O-acetyl-2-deoxy-6-O-sulfo-1-thio-2-(2,2,2-trichloroethoxycarbonylamino)-β-D-galactopyranosyl o-hexynylbenzoate, monosodium salt 6 (12.6 mg, 0.013 mmol) were dissolved in MeCN (126 μL) under an argon atmosphere. Activated MS-300 (12 mg) was added, and the mixture was stirred at room temperature for 1 hour. After cooling the reaction solution on ice, PPh$_3$AuNTf$_2$-0.5 Toluene (6 mg, 3.7 μmol) was added to start the reaction. The mixture was stirred at 0° C. for 15 min, and the reaction solution was applied as it was to a silica gel column. An ion peak of tetrasaccharide 12 was observed in mass spectrometry (yield approx. 5%). Also, it was confirmed by NMR analysis that the CH coupling constant (J value) of the anomeric site (position 1) of the glycosidic linkage sites formed by this reaction was $J_{CH}$=178 Hz, suggesting that the obtained tetrasaccharide was the compound 12 linked by an α bond. ESI-MS [M−H]$^-$ calcd for C$_{55}$H$_{67}$$^{35}$Cl$_6$N$_2$O$_{35}$S$_2$: 1589.1, found 1589.1.

(Synthesis Example 2) (Synthesis of Sulfated Tetrasaccharide)

The sulfated disaccharide donor 6 and the disaccharide acceptor 11 prepared as above were condensed according to the following reaction equation to prepare the target sulfated tetrasaccharide 13. The compound number shown after the name of a compound in a preparation example indicates the compound number shown in the following reaction equation.

[Formula 20]

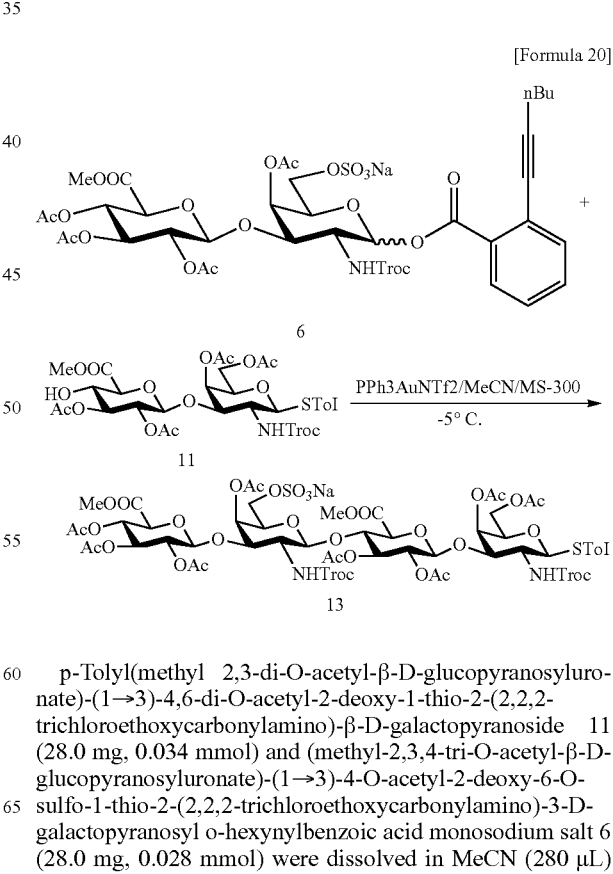

p-Tolyl(methyl 2,3-di-O-acetyl-β-D-glucopyranosyluronate)-(1→3)-4,6-di-O-acetyl-2-deoxy-1-thio-2-(2,2,2-trichloroethoxycarbonylamino)-β-D-galactopyranoside 11 (28.0 mg, 0.034 mmol) and (methyl-2,3,4-tri-O-acetyl-β-D-glucopyranosyluronate)-(1→3)-4-O-acetyl-2-deoxy-6-O-sulfo-1-thio-2-(2,2,2-trichloroethoxycarbonylamino)-3-D-galactopyranosyl o-hexynylbenzoic acid monosodium salt 6 (28.0 mg, 0.028 mmol) were dissolved in MeCN (280 μL)

under an argon atmosphere. Activated MS-300 (12 mg) was added, and the mixture was stirred at room temperature for 1 hour. After cooling the reaction solution to −5° C., PPh$_3$AuNTf$_2$-0.5 Toluene (13 mg, 8.4 μmol) was added to start the reaction. The mixture was stirred at −5° C. for 3 hours, and the reaction solution was applied as it was to a silica gel column. An ion peak of the tetrasaccharide 12 was observed in mass spectrometry (yield approx. 10%). Also, it was confirmed by NMR analysis that the J value of H-1 and H-2 of the glycosidic linkage sites formed by this reaction was $J_{1,2}$=8.3 Hz, suggesting that the obtained tetrasaccharide was the compound 13 linked by a β bond. ESI-MS [M−H]$^-$ calcd for $C_{55}H_{67}{}^{35}Cl_6N_2O_{35}S_2$: 1589.1, found 1589.1.

The invention claimed is:

1. A method of producing a saccharide having a sulfate group and/or a phosphate group, comprising:
   (a) a step of preparing a first saccharide having a non-protected sulfate group and/or a non-protected phosphate group and a second saccharide having a non-protected sulfate group and/or a non-protected phosphate group and
   (b) a step of condensing the first saccharide and the second saccharide prepared in the step (a) with each other in the presence of an acid and without the use of an enzyme.

2. The production method according to claim 1, wherein the first saccharide and the second saccharide are each a saccharide having a leaving group at a 1-position carbon atom of the saccharide and having a nucleophilic group.

3. The production method according to claim 1, wherein the first saccharide and the second saccharide are the same saccharide.

4. The production method according to claim 2, wherein the nucleophilic group is selected from a hydroxy group, an amino group, and a thiol group.

5. The production method according to claim 1, wherein the first saccharide and the second saccharide are each a saccharide constituting a 6-membered ring, and have a leaving group at a 1-position carbon atom of the saccharide, a nucleophilic group at least at any of positions 2, 3, 4, or 6 of the saccharide, and at least one non-protected sulfate group or non-protected phosphate group at least at any of positions 2, 3, 4, or 6 of the saccharide.

6. The production method according to claim 1, wherein the first saccharide and the second saccharide are each a saccharide constituting a 6-membered ring, and have a leaving group at a 1-position carbon atom of the saccharide, a nucleophilic group at least at any of position 3 or 4 of the saccharide, and a non-protected sulfate group or a non-protected phosphate group at least at any of positions 2, 4, or 6 of the saccharide.

7. The production method according to claim 1, wherein the first saccharide and the second saccharide are represented by the following formula:

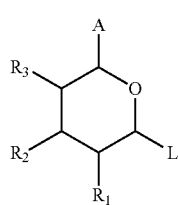

[Formula 1]

wherein
L is a leaving group;
A is selected from the group consisting of a hydrogen atom, a protected or non-protected carboxyl group, a protected or non-protected amide group, and —CH$_2$—R$_4$;
R$_1$ to R$_4$ are each independently selected from the group consisting of a hydrogen atom, a non-protected sulfate group, a non-protected phosphate group, a protected or non-protected hydroxy group, a protected or non-protected amino group, a protected or non-protected thiol group, and a saccharide residue;
at least one of R$_1$ to R$_4$ is a non-protected sulfate group or a non-protected phosphate group; and
at least one of R$_1$ to R$_4$ is a nucleophilic group selected from a hydroxy group, an amino group, and a thiol group.

8. The production method according to claim 7, wherein in the formula,
A is —CH$_2$—R$_4$;
R$_2$ to R$_4$ are selected from a non-protected sulfate group, a non-protected phosphate group, a protected or non-protected hydroxy group, and a saccharide residue,
provided that at least one of R$_2$ to R$_4$ is a non-protected sulfate group or a non-protected phosphate group; and
R$_1$ is a protected or non-protected amino group.

9. The production method according to claim 8, wherein the saccharide residue is a glucuronic acid residue.

10. The production method according to claim 8, wherein the saccharide residue is a glucuronic acid residue having a sulfate group at a 2-position carbon atom of the saccharide.

11. The production method according to claim 1, wherein the first saccharide and the second saccharide are represented by the following formula:

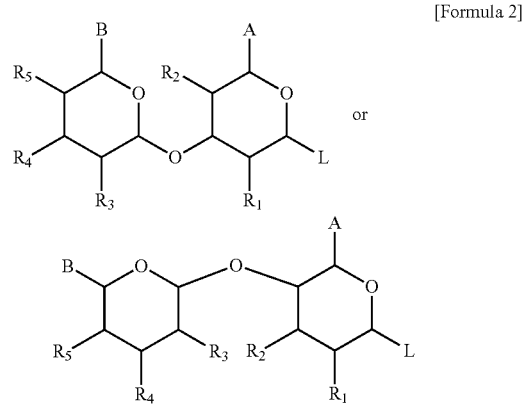

[Formula 2]

wherein
L is a leaving group;
A and B are each independently selected from the group consisting of a hydrogen atom, a protected or non-protected carboxyl group, a protected or non-protected amide group, and —CH$_2$—R$_6$;
R$_1$ to R$_6$ are each independently selected from the group consisting of a hydrogen atom, a non-protected sulfate group, a non-protected phosphate group, a protected or non-protected hydroxy group, a protected or non-protected amino group, a protected or non-protected thiol group, and a saccharide residue;

at least one of $R_1$ to $R_6$ is a non-protected sulfate group or a non-protected phosphate group; and at least one of $R_1$ to $R_6$ is a nucleophilic group selected from a hydroxy group, an amino group, and a thiol group.

12. The production method according to claim 11, wherein
in the formula,
A is —$CH_2$—$R_6$; and
B is a protected or non-protected carboxyl group;
$R_2$ to $R_6$ are each independently selected from a non-protected sulfate group, a non-protected phosphate group, and a protected or non-protected hydroxy group, and a saccharide residue,
provided that at least one of $R_2$ to $R_6$ is a non-protected sulfate group or a non-protected phosphate group; and
$R_1$ is a protected or non-protected amino group.

13. The production method according to claim 1, wherein the saccharide produced is a polysaccharide comprising 2 sugars (disaccharide) to 100 sugars (hectosaccharide).

14. The production method according to claim 1, wherein the saccharide produced is chondroitin sulfate or heparin sulfate.

15. A method of producing a compound comprising a saccharide having a sulfate group and/or a phosphate group, the method comprising:
(a1) a step of preparing a first saccharide having a non-protected sulfate group and/or a non-protected phosphate group and
(b1) a step of condensing the first saccharide prepared in the step (a1) with a compound having a nucleophilic group in the presence of an acid and without the use of an enzyme.

16. The production method according to claim 15, wherein the first saccharide is a saccharide having a leaving group at position 1 of the saccharide.

17. The production method according to claim 15 comprising:
(c1) a step of further condensing the compound comprising a saccharide having a sulfate group and/or a phosphate group" prepared in the step (b1) with
a compound selected from a saccharide having a non-protected sulfate group and/or a non-protected phosphate group, a compound having a nucleophilic group, and the compound comprising a saccharide having a sulfate group and/or a phosphate group prepared in the step (b1).

18. The production method according to claim 17, wherein the nucleophilic group is selected from a hydroxy group, an amino group, and a thiol group.

19. The production method according to claim 17, wherein the compound having a nucleophilic group is selected from a saccharide, an amino acid, a peptide, a protein, and a derivative thereof.

20. The production method according to claim 15, wherein the saccharide having a non-protected sulfate group and/or a non-protected phosphate group is a saccharide constituting a 6-membered ring, and has a leaving group at a 1-position carbon atom of the saccharide, has a nucleophilic group at least at any of positions 2, 3, 4, or 6 of the saccharide, and has at least one non-protected sulfate group or non-protected phosphate group at least at any of positions 2, 3, 4, or 6 of the saccharide.

21. The production method according to claim 15, wherein the first saccharide is a saccharide comprising a 6-membered ring, and has a leaving group at a 1-position carbon atom of the saccharide, has a nucleophilic group at least at any of positions 3 and 4 of the saccharide, and has a non-protected sulfate group or a non-protected phosphate group at least at any of positions 2, 4, or 6 of the saccharide.

22. The production method according to claim 15, wherein the first saccharide is a compound having a structure represented by the following formula:

[Formula 3]

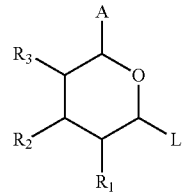

wherein
L is a leaving group;
A is selected from the group consisting of a hydrogen atom, a protected or non-protected carboxyl group, a protected or non-protected amide group, and —$CH_2$—$R_4$;
$R_1$ to $R_4$ are each independently selected from the group consisting of a hydrogen atom, a non-protected sulfate group, a non-protected phosphate group, a protected or non-protected hydroxy group, a protected or non-protected amino group, a protected or non-protected thiol group, and a saccharide residue;
at least one of $R_1$ to $R_4$ is a non-protected sulfate group or a non-protected phosphate group; and
at least one of $R_1$ to $R_4$ has a nucleophilic group selected from a hydroxy group, an amino group, and a thiol group.

23. The production method according to claim 22, wherein in the formula,
A is —$CH_2$—$R_4$;
$R_3$ is selected from a non-protected sulfate group, a non-protected phosphate group, a protected or non-protected hydroxy group, and a saccharide residue;
$R_4$ is selected from a non-protected sulfate group, a non-protected phosphate group, and a protected or non-protected hydroxy group;
provided that at least one of $R_4$ and $R_3$ is a non-protected sulfate group or a non-protected phosphate group;
$R_1$ is a protected or non-protected amino group; and
$R_2$ is a non-protected hydroxy group or a saccharide residue.

* * * * *

UNITED STATES PATENT AND TRADEMARK OFFICE
CERTIFICATE OF CORRECTION

PATENT NO. : 10,913,763 B2
APPLICATION NO. : 16/078861
DATED : February 9, 2021
INVENTOR(S) : Kajihara et al.

It is certified that error appears in the above-identified patent and that said Letters Patent is hereby corrected as shown below:

In the Specification

Column 10, Line 7: Please correct "$R_a$" to read -- $R_4$ --

Column 10, Line 61: Please correct "—$CH_Z$—$R_6$" to read -- —$CH_2$—$R_6$ --

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*